US009877684B2

(12) United States Patent
Banet et al.

(10) Patent No.: US 9,877,684 B2
(45) Date of Patent: Jan. 30, 2018

(54) PHYSIOLOGICAL MONITORING SYSTEM FEATURING FLOORMAT AND WIRED HANDHELD SENSOR

(71) Applicant: TOSENSE, INC., La Jolla, CA (US)

(72) Inventors: Matthew Banet, San Diego, CA (US); Marshal Singh Dhillon, San Diego, CA (US); Susan Meeks Pede, Encinitas, CA (US); Lauren Nicole Miller Hayward, San Diego, CA (US); Arthur Deptala, Santee, CA (US); Jonas Dean Cochran, Santee, CA (US); Mark Singh Dhillon, San Diego, CA (US)

(73) Assignee: TOSENSE, INC., La Jolla, CA (US)

( * ) Notice: Subject to any disclaimer, the term of this patent is extended or adjusted under 35 U.S.C. 154(b) by 0 days.

(21) Appl. No.: 14/988,731

(22) Filed: Jan. 5, 2016

(65) Prior Publication Data

US 2017/0188968 A1    Jul. 6, 2017

(51) Int. Cl.
*A61B 5/02* (2006.01)
*A61B 5/00* (2006.01)
*A61B 5/024* (2006.01)
*A61B 5/0452* (2006.01)
*A61B 5/053* (2006.01)
(Continued)

(52) U.S. Cl.
CPC .......... *A61B 5/6892* (2013.01); *A61B 5/0008* (2013.01); *A61B 5/02427* (2013.01); *A61B 5/0452* (2013.01); *A61B 5/053* (2013.01); *A61B 5/0809* (2013.01); *A61B 5/14552* (2013.01); *A61B 5/4872* (2013.01); *A61B 5/7275* (2013.01); *A61B 5/7282* (2013.01); *A61B 5/742* (2013.01)

(58) Field of Classification Search
CPC . A61B 5/6892; A61B 5/0008; A61B 5/02427; A61B 5/0452; A61B 5/053; A61B 5/0809; A61B 5/14552; A61B 5/4872; A61B 5/7275; A61B 5/7282; A61B 5/742
See application file for complete search history.

(56) References Cited

U.S. PATENT DOCUMENTS

2014/0330142 A1*  11/2014  Banet .................. A61B 5/0205
                                                              600/484
2015/0257680 A1*   9/2015  Inan .................... A61B 5/7207
                                                              600/301

* cited by examiner

*Primary Examiner* — George Manuel
(74) *Attorney, Agent, or Firm* — Acuity Law Group, PC; Michael A. Whittaker

(57) ABSTRACT

A physiological monitoring system features a Floormat and Handheld Sensor connected by a cable. A user stands on the Floormat and grips the Handheld Sensor. These components measure time-dependent physiological waveforms from a user over a conduction pathway extending from the user's hand or wrist to their feet. The Handheld Sensor and Floormat use a combination of electrodes that inject current into the user's body and collect bioelectric signals that, with processing, yield ECG, impedance, and bioreactance waveforms. Simultaneously, the Handheld Sensor measures photoplethysmogram waveforms with red and infrared radiation and pressure waveforms from the user's fingers and wrist, while the Floormat measures signals from load cells to determine 'force' waveforms to determine the user's weight, and ballistocardiogram waveforms to determine parameters related to cardiac contractility. Processing these waveforms with algorithms running on a microprocessor yield the vital sign, hemodynamic, and biometric parameters.

30 Claims, 10 Drawing Sheets

(51) Int. Cl.
  *A61B 5/1455* (2006.01)
  *A61B 5/08* (2006.01)

PHYSIOLOGICAL MONITORING SYSTEM FEATURING FLOORMAT AND WIRED HANDHELD SENSOR

BACKGROUND AND FIELD OF THE INVENTION

1. Field of the Invention

The invention relates to sensors that measure physiological signals from a patient (e.g. a user), and the use of such sensors.

2. General Background

Physiological sensors, such as vital sign monitors, typically measure signals from a user to determine time-varying waveforms, e.g. thoracic bio-impedance (TBI), bio-reactance (BR), and electrocardiogram (ECG) waveforms, with electrodes that attach to the user's skin. These waveforms can be processed/analyzed to extract other medically relevant parameters such as heart rate (HR) and heart rate variability (HRV), respiration rate (RR), stroke volume (SV), cardiac output (CO), and information relating to thoracic fluid content, e.g. thoracic fluid index (TFC) and general body fluids (Fluids). Certain physiological conditions can be identified from these parameters using one-time measurements; other conditions require observation of time-dependent trends in the parameters in order to identify the underlying condition. In all cases, it is important to measure the parameters with high repeatability and accuracy.

Some conditions require various physiological parameters to be measured over a relatively short period of time in order to identify the condition. For example, Holter monitors can characterize various types of cardiac arrhythmias by measuring HR, HRV, and ECG waveforms over periods ranging from a day to a few weeks. On the other hand, chronic diseases such as congestive heart failure (CHF) and end-stage renal disease (ESRD) typically require periodic measurements of Fluids and weight throughout the user's life in order to identify the condition. Not surprisingly, user compliance with measurement routines typically decreases as the measurement period increases. This is particularly true when measurements are made outside of a conventional medical facility, e.g., at the user's home or in a residential facility such as a nursing home.

Furthermore, the measured values of some physiological parameters will vary with the location at which the parameters are measured, while those associated with other physiological parameters are relatively independent of the location at which the parameters are measured. For example, parameters such as HR, which depends on the time-dependent variation of R-R intervals associated with QRS complexes in ECG waveforms, are relatively insensitive to sensor positioning. Likewise, pulse oximetry (SpO2) and pulse rate (PR), as measured from photoplethysmogram (PPG) waveforms with a pulse oximeter, show little variance with measurement location.

On the other hand, measurements that depend on amplitude-dependent features in waveforms, such as TFC or Fluids, will be strongly dependent on the measurement location, e.g. the positioning of electrodes. In the case of TFC, for example, the measured value depends strongly on the sensed impedance between a set of electrodes. And this, in turn, will vary with the electrodes' placement. TFC deviation in the day-to-day placement of the electrodes can result in measurement errors. This, in turn, can lead to misinformation (particularly when trends of the measured parameters are to be extracted), thereby nullifying the value of such measurements and thus negatively impacting treatment.

Like TFC, measured values of blood pressure (BP), such as systolic (SYS), diastolic (DIA), and pulse (PP) pressures are typically sensitive to the location at which the parameter is measured. For example, blood pressure measured at the brachial artery with a sphygmomanometer (i.e. a manual blood pressure cuff) or with an oscillometric device (i.e. an automated blood pressure cuff measuring oscillometric waveforms) will typically be different from that measured at other locations on the body, such as the wrist, thigh, finger, or even the opposite arm. Mean arterial pressure (MAP) is less sensitive to position, as it is relatively constant throughout the body. Body (e.g. skin) temperature is similarly dependent on the location at which it is measured, although core temperature (TEMP), as measured from the ear or mouth, is relatively consistent.

3. Sensors, Devices, and Relevant Physiology

Disposable electrodes that measure ECG and TBI waveforms are typically worn on the user's chest or legs and include: i) a conductive hydrogel that contacts the user's skin; ii) an Ag/AgCl-coated eyelet that contacts the hydrogel; iii) a conductive metal post that connects to a lead wire or cable extending from the sensing device; and iv) an adhesive backing that adheres the electrode to the user. Unfortunately, during a measurement, the lead wires can pull on the electrodes if the device is moved relative to the user's body, or if the user ambulates and snags the lead wires on surrounding objects. Such pulling can be uncomfortable or even painful, particularly where the electrodes are attached to hirsute parts of the body, and this can inhibit user compliance with long-term monitoring. Moreover, these actions can degrade or even completely eliminate adhesion of the electrodes to the user's skin, and in some cases completely destroy the electrodes' ability to sense the physiological signals at various electrode locations.

Some devices that measure ECG and TBI waveforms are worn entirely on the user's body. These devices have been developed to feature simple, patch-type systems that include both analog and digital electronics connected directly to underlying electrodes. Such devices, like the Holter monitors described above, are typically prescribed for relatively short periods of time, e.g. for a period of time ranging from a day to several weeks. They are typically wireless and include features such as Bluetooth® transceivers to transmit information over a short distance to a second device, which then transmits the information via a cellular radio to a web-based system.

SpO2 values are almost always measured at the user's fingers, earlobes, or, in some cases, the forehead. In these cases, users wear an optical sensor to measure PPG waveforms, which are then processed to yield SpO2 and PR values. TEMP is typically measured with a thermometer inserted into the user's mouth, or with an optical sensor featuring an infrared-sensitive photodiode pointed into the user's ear.

Assessing Fluids. TFC, weight, and hydration status is important in the diagnosis and management of many diseases. For example, ESRD occurs when a user's kidneys are no longer able to work at a level needed for day-to-day life. The disease is most commonly caused by diabetes and high blood pressure, and is characterized by swings in SYS and DIA along with a gradual increase in Fluids throughout the body. Users suffering from ESRD typically require hemodialysis or ultrafiltration to remove excess Fluids. Thus, accurate measurement of this parameter and/or TFC to characterize ESRD can eliminate the need for empirical clinical estimations that often lead to over-removal or under-removal of fluids during dialysis, thereby preventing hemodynamic instability and hypotensive episodes (Anand et al., "*Monitoring Changes in Fluid Status With a Wireless Multisensor Monitor: Results From the Fluid Removal During Adherent Renal Monitoring (FARM) Study*," Congest Heart Fail. 2012; 18:32-36). A similar situation exists with respect to CHF, which is a complicated disease typically monitored using a "constellation" of physiological factors, e.g., fluid status (e.g. Fluids, TFC), vital signs (i.e., HR, RR, TEMP, SYS, DIA, and SpO2), and hemodynamic parameters (e.g. CO, SV). Accurate measurement of these parameters can aid in managing users, particularly in connection with dispensing diuretic medications, and thus reduce expensive hospital readmissions (Packer et al., "*Utility of Impedance Cardiography for the Identification of Short-Term Risk of Clinical Decompensation in Stable Users With Chronic Heart Failure*," J Am Coll Cardiol 2006; 47:2245-52).

CHF is a particular type of heart failure (HF), which is a chronic disease driven by complex pathophysiology. In general terms, HF occurs when SV and CO are insufficient to adequately perfuse the kidneys and lungs. Causes of this disease are well known and typically include coronary heart disease, diabetes, hypertension, obesity, smoking, and valvular heart disease. In systolic HF, ejection fraction (EF) can be diminished (<50%), whereas in diastolic HF this parameter is typically normal (>65%). The common signifying characteristic of both forms of heart failure is time-dependent elevation of the pressure within the left atrium at the end of its contraction cycle, or left ventricular end-diastolic pressure (LVEDP). Chronic elevation of LVEDP causes transudation of fluid from the pulmonary veins into the lungs, resulting in shortness of breath (dyspnea), rapid breathing (tachypnea), and fatigue with exertion due to the mismatch of oxygen delivery and oxygen demand throughout the body. Thus, early compensatory mechanisms for HF that can be detected fairly easily include increased RR and HR.

As CO is compromised, the kidneys respond with decreased filtration capability, thus driving retention of sodium and water and leading to an increase in intravascular volume. As the LVEDP rises, pulmonary venous congestion worsens. Body weight increases incrementally, and fluids may shift into the lower extremities. Medications for HF are designed to interrupt the kidneys' hormonal responses to diminished perfusion, and they also work to help excrete excess sodium and water from the body. However, an extremely delicate balance between these two biological treatment modalities needs to be maintained, since an increase in blood pressure (which relates to afterload) or fluid retention (which relates to preload), or a significant change in heart rate due to a tachyarrhythmia, can lead to decompensated HF. Unfortunately, this condition is often unresponsive to oral medications. In that situation, admission to a hospital is often necessary for intravenous diuretic therapy.

In medical centers, HF is typically detected using Doppler/ultrasound, which measures parameters such as SV, CO, and EF. In the home environment, on the other hand, gradual weight gain measured with a simple weight scale is likely the most common method used to identify CHF. However, by itself, this parameter is typically not sensitive enough to detect the early onset of CHF—a particularly important stage when the condition may be ameliorated simply and effectively by a change in medication or diet.

SV is the mathematical difference between left ventricular end-diastolic volume (EDV) and end-systolic volume (ESV), and represents the volume of blood ejected by the left ventricle with each heartbeat; a typical value is about 70-100 mL. CO is the average, time-dependent volume of blood ejected from the left ventricle into the aorta and, informally, indicates how efficiently a user's heart pumps blood through their arterial tree; a typical value is about 5-7 L/min. CO is the product of HR and SV.

CHF users—particular those suffering from systolic HF—may receive implanted devices such as pacemakers and/or cardioverter-defibrillators to increase EF and subsequent blood flow throughout the body. These devices may include circuitry and algorithms to measure the electrical impedance between different leads of the device. Some implanted devices process this impedance to calculate a "fluid index". As thoracic fluid increases in the CHF user, the impedance typically is reduced, and the fluid index increases.

4. Clinical Solutions

Many of the above-mentioned parameters can be used as early markers or indicators that signal the onset of CHF. EF is typically low in users suffering from this chronic disease, and it can be further diminished by factors such as a change in physiology, an increase in sodium in the user's diet, or non-compliance with medications. This is manifested by a gradual decrease in SV, CO, and SYS that typically occurs between two and three weeks before hospitalization becomes necessary to treat the condition. As noted above, the reduction in SV and CO diminishes perfusion to the kidneys. These organs then respond with a reduction in their filtering capacity, thus causing the user to retain sodium and water and leading to an increase in intravascular volume. This, in turn, leads to congestion, which is manifested to some extent by a build-up of fluids in the user's thoracic cavity (e.g. TFC). Typically, a detectable increase in TFC occurs about 1-2 weeks before hospitalization becomes necessary. Body weight increases after this event (typically by between three and five pounds), thus causing fluids to shift into the lower extremities. At this point, the user may experience an increase in both HR and RR to increase perfusion. Nausea, dyspnea, and weight gain typically grow more pronounced a few days before hospitalization becomes necessary. As noted above, a characteristic of decompensated HF is that it is often unresponsive to oral medications; thus, at this point, intravenous diuretic therapy in a hospital setting often becomes mandatory. A hospital stay for intravenous diuretic therapy typically lasts about 4 days (costing several thousands of dollars per day, or more), after which the user is discharged and the above-described cycle may start over once again.

Such cyclical pathology and treatment is physically taxing on the user, and economically taxing on society. In this regard, CHF and ESRD affect, respectively, about 5.3 million and 3 million Americans, resulting in annual healthcare costs estimated at $45 billion for CHF and $35 billion for ESRD. CHF users account for approximately 43% of annual Medicare expenditures, which is more than the combined expenditures for all types of cancer. Somewhat disconcertingly, roughly $17 billion of this is attributed to hospital readmissions. CHF is also the leading cause of mortality for users with ESRD, and this demographic costs Medicare nearly $90,000/user annually. Thus, there understandably exists a profound financial incentive to keep users suffering from these diseases out of the hospital. Starting in 2012, U.S. hospitals have been penalized for above-normal readmission rates. Currently, the penalty has a cap of 1% of payments, growing to over 3% in the next 3 years.

Of some promise, however, is the fact that CHF-related hospital readmissions can be reduced when clinicians have access to detailed information that allows them to remotely titrate medications, monitor diet, and promote exercise. In fact, Medicare has estimated that 75% of all users with ESRD and/or CHF could potentially avoid hospital readmissions if treated by simple, effective programs.

Thus, in order to identify precursors to conditions such as CHF and ESRD, physicians can prescribe physiological monitoring regimens to users living at home. Typically, such regimens require the use of multiple standard medical devices, e.g. blood pressure cuffs, weight scales, and pulse oximeters. In certain cases, users use these devices daily and in a sequential manner, i.e., one device at a time. The user then calls a central call center to relay their measured parameters to the call center. In more advanced systems, the devices are still used in a sequential manner, but they automatically connect through a short-range wireless link (e.g. a Bluetooth® system) to a "hub," which then forwards the information to a call center. Often, the hub features a simple user interface that presents basic questions to the user, e.g. questions concerning their diet, how they are feeling, and whether or not medications were taken.

Ultimately, however, and regardless of how sophisticated such instrumentation may be, in order for such monitoring to be therapeutically effective, it is important for the user to be compliant and use their equipment consistently. Poor compliance (e.g. less-than-satisfactory consistency) with the use of any medical device may be particularly likely in an environment such as the user's home or a nursing home, where direct supervision may be less than optimal. Of course, the clinical usefulness of any monitoring approach requires that the physiological parameters it measures be accurate.

SUMMARY OF THE INVENTION

In view of the foregoing, it would be beneficial to provide a monitoring system that is suitable for home use. Particularly valuable would be a single system, free of external components, that is wireless and conveniently measures a collection of vital signs and hemodynamic parameters. Ideally, such a system would feature a single device and only reusable (i.e. no disposable) sensors. The device should be easy to use and feature a simple form factor that integrates into the user's day-to-day activities. The monitoring system according to the invention, which facilitates monitoring conditions such as HF, CHF, ESRD, cardiac arrhythmias, and other diseases, is designed to achieve this very goal.

More specifically, the invention described herein is a system that features a Floormat and Handheld Sensor, electrically connected to each other by a flexible, conductor-bearing cable, that operate in concert with the user's mobile device. The cable-connected configuration facilitates measurement of various physiological parameters over a measurement pathway that is as long as possible. This, in turn, yields time-dependent waveforms with high signal-to-noise ratios and, ultimately, accurate physiological information.

The Floormat resembles a conventional bathroom scale. It connects through the cable to the Handheld Sensor, which features a grip that the user can easily hold while standing on the Floormat. Collectively these components measure an enhanced set of parameters that include: all vital signs (e.g. PR and/or HR, SpO2, RR, SYS, MAP, and DIA, and TEMP); hemodynamic parameters (SV, CO, Fluids); and biometric parameters (weight, body composition). The system transmits information through a wireless interface to a web-based system, where a clinician can analyze it to help diagnose a user.

The system—which is a combination of the Floormat and Handheld Sensor—measures time-dependent PPG, pressure, ECG, TBI, and/or BR waveforms easily and conveniently from a user. It processes these waveforms to determine the above-mentioned parameters. During operation, the user simply stands on the Floormat and holds or otherwise supports the Handheld Sensor with (or in the region of) either the left or right hand. This establishes an electrical conduction pathway that extends from the user's hand and/or wrist to their feet. Over this pathway, the Handheld Sensor and Floormat use a combination of electrodes that inject current into the user's body, and subsequently sense bioelectric signals that, with processing, yield ECG, TBI, and BR waveforms. Simultaneously, the Handheld Sensor measures PPG waveforms with both red and infrared radiation (PPG-RED, PPG-IR) and pressure waveforms from the user's fingers and wrist, while the Floormat measures signals from embedded load cells to determine 'force' waveforms to measure the user's weight, and ballistocardiogram (BCG) waveforms. BCG waveforms, in turn, can be processed to estimate parameters related to cardiac contractility. Thus, with just a single device, the system measures the following synchronized, time-dependent waveforms: ECG, TBI, BR, PPG-RED, PPG-IR, force, and BCG. Processing these waveforms with algorithms running on a microprocessor yields the vital sign, hemodynamic, and biometric parameters described above. Clinicians can analyze these parameters, which the system sends wirelessly to a web-based system, to diagnose a user in their home environment. In this and other ways, the combined Floormat and Handheld Sensor provides an effective tool for characterizing users with chronic diseases, such as CHF, ESRD, and hypertension.

The Floormat and Handheld Sensor are designed, respectively, to resemble a conventional bathroom scale and a hand-held grip used, e.g., in a conventional video game controller. Most users are familiar with such devices, and thus use of the system should be intuitive. To make measurements, the user only needs to step on the Floormat and grip the Handheld Sensor. Total measurement time is about 30-60 seconds, after which a simple user interface featuring, e.g., light-emitting diodes (LEDS) and/or a vibrating 'buzzer' indicates the measurement is complete and that the user can step off the Floormat and release the Handheld Sensor. Such ease of use may increase compliance, which in turn yields the daily measurements that are required to diagnose and effectively treat most chronic diseases.

In one aspect, the invention provides a system for measuring a user's CO value. The system features: 1) a Floormat configured to rest on a flat surface and supporting at least two electrodes and at least one load cell, wherein the load cell is further configured to generate a force waveform; and 2) a Handheld Sensor connected to the Floormat through a cable and featuring at least two electrodes. Within either the Handheld Sensor or the Floormat (or both) is a circuit board including an analog impedance system connected to the electrodes. The analog impedance system is configured to inject electrical current into the user through one electrode in the Floormat and one electrode in the Handheld Sensor, sense signals through separate electrodes in the Floormat and Handheld Sensor, and in response generate both impedance and ECG waveforms.

A first processing system (e.g., a microprocessor running computer code) in the system processes a digitized version of the force waveform to determine a weight value. A second processing system then processes a digitized version of the impedance waveform to determine an impedance pulse, and further processes the impedance pulse and the weight value to determine a SV value, as is described in detail below. A third processing system processes a digitized version of the ECG waveform to determine an ECG pulse, and then further processes the ECG pulse to determine an HR value. And finally, a fourth processing system collectively processes the SV and HR values to determine the CO value.

In embodiments, the Floormat's electrodes are disposed on a top surface so that they contact the user's foot when the user stands on the Floormat. The Handheld Sensor's electrodes are disposed on a grip connected to the Handheld Sensor so that they contact the user's hand when the user holds the Handheld Sensor. Thus, when the user operates the system, they have electrodes contracting their hands and feet. Suitably, electrodes in both the Floormat and Handheld Sensor include at least one of the following: a conductive fabric, a metal, a conductive foam, a hydrogel material, a conductive ink, a conductive rubber.

In other embodiments, the cable is flexible and includes a set of conducting wires that connect electrodes in the Handheld Sensor and/or Floormat to the analog impedance system, which as described above is typically included on a circuit board enclosed by one (or both) of these components. In embodiments, the cable is a retractable cable that retracts into the Floormat.

Different algorithms may be run by the system according to the invention. Typically, such algorithms are operated by compiled computer code running on a microprocessor disposed on a circuit board within the system. For example, in one embodiment, the algorithm operates on the first processing system to calculate a volume conductor ($V_c$) from an inverse of the weight value. Another algorithm runs on the second processing system to calculate a left ventricular ejection time from the impedance pulse. Additionally, the second processing system calculates $(d\Delta Z/dt)_{max}$ from the impedance pulse, and $Z_0$ from the baseline of the impedance waveform. Using these parameters, the first processing system calculates SV from equations similar to those described in more detail below, or mathematical equivalents thereof.

In other embodiments, an algorithm operating on the third processing system analyzes the ECG pulse to determine an ECG QRS complex from which it calculates HR. Finally, an algorithm operating on the fourth processing system calculates the CO value from a product of the SV and HR.

In another aspect, the invention provides a system for measuring a ballistocardiogram pulse from a user. The system features a Floormat and Handheld Sensor similar to those described above. It also includes an analog ECG system, connected to an electrode and an electrode in the Handheld Sensor, which generates an ECG waveform from signals sensed through these electrodes. The system features three processing systems, each running algorithms as described above. The first processing system processes a digitized version of the ECG waveform to determine an ECG pulse, the second processing system process the force waveform to determine a ballistocardiogram waveform, and the third processing system collectively processes the ECG pulse and the ballistocardiogram waveform to determine the ballistocardiogram pulse.

In embodiments, the ECG pulse determined by the first processing system is a collection of ECG QRS complexes, and the third processing system determines a first time segment associated with a time separating a first point in time corresponding to a first ECG QRS complex, and a second point in time corresponding to a second ECG QRS complex. Suitably, the R-wave of the first ECG QRS complex directly precedes the R-wave from the second ECG QRS complex, and the R-waves of the first and second ECG QRS complexes are separated in time by a period associated with a single heartbeat. The third processing system determines a second time segment associated with a time separating a third point in time corresponding to a third ECG QRS complex, and a fourth point in time corresponding to a fourth ECG QRS complex. Once these time segments are determined, the third processing system collectively processes corresponding segments of the BCG waveform to determine the BCG pulse. For example, the third processing system can sum (e.g. add) or average these segments to generate the ballistocardiogram pulse. In still other embodiments, the system can include a fourth processing system that process parameters associated with the BCG pulse and a calibration factor to estimate parameters such as cardiac contractility, SV, CO, HR, and ejection fraction. The calibration factor, for example, can be determined from a large population study wherein BCG pulses and the above-mentioned parameters are measured with known reference techniques, and then analyzed with a mathematical model to determine the factor.

In another aspect, the invention provides a system for measuring a BP value from a user featuring a Floormat and Handheld Sensor similar to those described above. The system features analog ECG, optical, and pressure systems that measure, respectively, ECG, PPG, and pressure waveforms from the user. First and second processing systems process digitized versions of the ECG and PPG waveforms to determine pulses that are collectively processed with a third processing system to determine a transit time. A fourth processing system processes the pressure waveform to determine a BP calibration. And a fifth processing system processes the transit time and the BP calibration to determine the blood pressure value.

In embodiments, the first processing system determines a first time value corresponding to an ECG QRS complex within the ECG pulse, and the second processing system determines a second time value corresponding to the PPG pulse. For example, the system can determine the second time value from the base, maximum amplitude, maximum slope, and/or maximum of first mathematical derivative of the PPG pulse. In embodiments, the third processing system determines the transit time from the mathematical difference between the second and first time values. The fourth processing system processes the pressure waveform to determine MAP, SYS, and/or DIA, and additionally a patient-specific relationship between blood pressure and transit time. The blood pressure calibration can be determined from these values. In embodiments, the fifth processing system multiplies the transit time by the patient-specific relationship between blood pressure and transit time to determine BP. Alternatively, the fifth processing system can add SYS to the product of the patient-specific relationship between blood pressure and transit time to determine BP.

In another aspect, the invention provides a system that can be used, for example, to measure ECG and HR from a user.

The invention included a generally flat Floormat configured to rest stably on a generally flat surface and to support the weight of a user standing on it. The Floormat has a first electrode disposed at an upper surface thereof and in position to make contact with the sole of one of the user's feet when the user stands on the Floormat. The invention also includes a Handheld Sensor configured to be supported at a region of one of the user's hands. The Handheld Sensor includes a second electrode disposed in position to make contact with skin in the region of the user's hand when it is held, and is connected to the Floormat through a cable having one or more internal electrical conductors. The system further includes an analog system configured to receive biometric signals from the first and second electrodes and to process them to generate an analog physiological waveform. A digital system is configured to digitize the analog physiological waveform and to process it with computer code to determine the physiological parameter. The analog system is located in either the Floormat or the Handheld Sensor. Electrodes connect to the analog system by means of the electrical conductors in the cable. This configuration facilitates obtaining signals across a conduction pathway that is substantially as long as possible.

In embodiments, the sensor system uses differential amplifiers to generate analog waveforms, which include heartbeat-induced pulsations, e.g., ECG waveforms. HR can be determined from successive QRS complexes in the ECG waveforms. A processing system, i.e., a microprocessor and computer code that is executed on it, is located on a circuit board, which may be located in either the Floormat or the Handheld Sensor.

The Floormat suitably includes a load cell-based weight measurement system, to determine the user's weight.

The Handheld Sensor may include a grip by means of which the user can hold/support the Handheld Sensor, and one or more electrodes may be located in the grip so that they contact the user's palm and/or anterior (i.e., palm-side) surfaces of the user's fingers when the user holds the grip. Alternatively, the Handheld Sensor may include an arm-receiving portion, which could be as simple as a ring-shaped portion to encircle and be supported by the user's wrist without need for a grip, or it could be formed as a pair of "wings" extending from a base portion from which a grip extends. In this case, an inflatable pressure cuff is suitably provided in the arm-receiving portion to measure BP mechanically (i.e., by sensing and analyzing actual pressure values and/or waveforms), and the cuff could be configured to encircle the user's wrist (in the case of a ring-shaped arm-receiving portion). Alternatively, the inflatable pressure cuff could be configured as two opposing inflatable bladders that face each across a wrist-receiving space within the arm-receiving portion. The electrode would then be provided as an inflatable electrode, e.g., by providing elastically stretchable, electrically conductive material over the inflatable bladder(s).

In another aspect, the invention provides a system for monitoring SV from a user. The system includes a generally flat Floormat configured to rest stably on a generally flat surface and to support the weight of a user standing on it. The Floormat includes first and second electrodes disposed at an upper surface thereof, which are positioned (e.g., exposed at the upper surface) to make contact with the sole of one of the user's feet when the user stands on the Floormat. The system further includes a Handheld Sensor configured to be supported at a region of one of the user's hands (e.g., grasped by the hand or simply encircling the wrist akin to a bracelet). The Handheld Sensor includes third and fourth electrodes disposed in position to contact with skin in the region of the user's hand when it is held. In this case, the Handheld Sensor is electrically connected to the Floormat through a cable having one or more electrical conductors disposed therein.

The first and third electrodes are configured to inject electrical current into the user at their respective points of contact, and the second and fourth electrodes are configured to sense first and second biometric signals, respectively, which are induced by the injected electrical current. The biometric sensor system further includes a first analog system configured to receive the first and second biometric signals and to process them to generate first and second analog physiological waveforms, and a digital system configured to digitize the analog physiological waveforms and to process them with computer code to determine a physiological parameter such as SV.

In embodiments, the system features an impedance-measuring system comprised by the four electrodes and differential amplifiers to measure a set of analog impedance values that are digitized and processed to form a TBI or BR waveform having heartbeat-induced pulsations. A processing system that can be part of the Floormat or the Handheld Sensor receives a weight value from the Floormat and the TBI or BR waveforms and then processes this information to calculate SV.

Furthermore, the system may operate by calculating a derivative $d\Delta Z(t)/dt$ of an impedance waveform and determining a maximum value of the $d\Delta Z(t)/dt$ waveform; an area of a pulse in the $d\Delta Z(t)/dt$ waveform; an ejection time from the $d\Delta Z(t)/dt$ waveform; a maximum value of the $d\Delta Z(t)/dt$ waveform $((d\Delta Z(t)/dt)_{max})$; a left ventricular ejection time (LVET) from the $d\Delta Z(t)/dt$ waveform; and a baseline impedance $Z_0$. SV may then be determined from the equation:

$$SV = V_c \times \frac{(d\Delta Z(t)/dt)_{max}}{Z_o} \times LVET$$

where $V_c$ is a volume conductor, as described above, that may be calculated from a weight value that is suitably obtained via a load cell-based system in the Floormat. Alternatively, stroke volume may be determined from the equation:

$$SV = V_c \times \sqrt{\frac{(d\Delta Z(t)/dt)_{max}}{Z_o}} \times LVET$$

where, $V_c$ is the volume conductor described above.

In another aspect, the invention provides a system for measuring SpO2 featuring a Handheld Sensor with optical components; a Floormat system with circuit components for processing signals from the optical components; and a cable electrically connecting the Floormat and the Handheld Sensors. The Floormat includes a first electrode disposed at an upper surface thereof and in position to make contact with the sole of one of the user's feet when the user stands on the Floormat. The Handheld Sensor includes a second electrode that contacts skin in the region of the user's hand (i.e., palm-facing surfaces of the fingers or the wrist) when it is held; and a finger-receiving portion featuring an opening that receives the user's finger (typically located on the hand grasping the Sensor). Within the opening is an optical system that includes a first light source configured to irradiate the received finger and a photodetector configured to receive radiation after it irradiates the received finger.

The inventive system according to this aspect of the invention further includes a first analog system configured to receive biometric signals from the first electrode and from the second electrode and to process the biometric signals to generate a first analog physiological waveform; a second analog system configured to receive signals from the photodetector and to process them to generate a second analog physiological waveform; a first digital system configured to digitize the first analog physiological waveform and to process it with computer code to determine a first physiological parameter in the set of physiological parameters; and a second digital system configured to digitize the second analog physiological waveform and to process it with computer code to determine a second physiological parameter in the set of physiological parameters. The first analog system is located in either the Floormat or the Handheld Sensor and the electrode disposed in the other device is electrically connected to the first analog system by means of the electrical conductors in the cable.

In embodiments, the system may be configured to generate and analyze PPG waveforms, which include heartbeat-induced pulses. For example, computer code can identify the time between pulses in the PPG waveform to determine the user's PR. Furthermore, computer code may be configured to determine AD and DC components within the PPG waveform (including for red and infrared light wavelengths) and, from those components, a value of SpO2.

In yet another aspect, the invention provides a system for measuring a user's BP, e.g. SYS, MAP, and DIA. To that end, the system is configured generally as per the aspect of the invention described immediately above. The system includes a first analog system configured to receive biometric signals from the first electrode and from the second electrode and to process the biometric signals to generate one of a bioimpedance and a bioreactance signal that, with further processing, yields a first time-dependent physiological waveform. The system further includes systems to process signals from the photodetector to generate a second physiological waveform and to process the first and second waveforms to determine the user's BP.

In yet another aspect, the invention features a system configured to measure BP using an inflatable bladder, e.g., via oscillometry. Here, the system features a Floormat and Handheld Sensor similar to that described above. Either component may include a microprocessor-based pressure-control inflation system including a pressure sensor that senses air pressure in the inflatable cuff; an air pump; and a valve, with the pressure-control inflation system being configured and arranged to control inflation and deflation of the inflatable bladder and the air pump being connected to the inflatable cuff via a tube extending along the cable member to the inflatable cuff. The biometric sensor system further includes a first analog system configured to receive signals from the pressure sensor and to process them to generate pressure signals; and a processing system configured 1) to issue computer commands to the pressure-control system to inflate and deflate the cuff while the first analog system generates the pressure signals, and 2) to analyze modulations in digital versions of the pressure signals to estimate SYS, MAP, and DIA.

In embodiments, the system includes computer code that filters the pressure signal and identifies oscillations therein. For example, the oscillation having a maximum amplitude value typically corresponds to MAP; oscillations having predetermined ratios when normalized by the maximum amplitude typically correspond to SYS and DIA. Furthermore, the cuff may be provided in an arm-receiving portion of the Handheld Sensor, either as inflatable bladders that face each other across a wrist-receiving space in the arm-receiving portion or as an inflatable bladder disposed around an arm-encircling annular ring.

Suitably, the embodiments include electrodes on the upper surface of the Floormat and within the Handheld Sensor to facilitate measuring an ECG signal. HR can be determined from the time difference between successive QRS complexes in the ECG signal. Electrodes in the Handheld Sensor can be located on a grip that supports the Sensor, or as inflatable electrodes provided by means of elastically stretchable, conductive material that is stretched across a pair of inflatable bladders on opposing sides of the wrist-receiving space.

In yet another aspect, the invention features a system configured to measure BP using an inflatable bladder, e.g., via arterial occlusion. Here, the Handheld Sensor includes an optical system that measures a PPG waveform from the user's fingers, and an inflation system featuring an inflatable cuff that applies pressure to the corresponding wrist. Gradual inflation of the cuff compromises blood flow to the fingers, thereby describing amplitudes of pulsations within the PPG waveforms. Analysis of the pulsations with analog and digital systems yields BP values, particularly MAP and SYS.

In embodiments, the system includes computer code configured to analyze pulsatile pressure signals to identify systolic pressure based on an amplitude of the pressure wave having a minimum value, where the pressure wave amplitudes may be estimated from a mathematical function. The system may also include computer code configured to analyze pulsatile pressure signals to identify mean arterial pressure based on an amplitude of the pressure wave having a maximum value, where the pressure wave amplitudes may be estimated from a mathematical function.

According to another aspect, the invention features a sensor configured to measure a physiological parameter using a BCG signal generated from the user's feet, with QRS complexes in an ECG signal being used to identify fiducial points on the BCG signal. Thus, according to this aspect of the invention, a biometric sensor system includes a generally flat floormat configured to rest stably on a generally flat surface and to support the weight of a user standing thereon, which includes a weight-measuring system having at least one load cell and an amplifier system configured to measure a time-dependent load-cell voltage from at least one load cell and to process the time-dependent load-cell voltage to determine a time-dependent load-cell waveform; and a first electrode disposed at an upper surface of the floormat and in position to make contact with the sole of one of the user's feet when the user stands on the floormat. The system further includes a handheld sensor configured to be supported at a region of one of the user's hands, which includes a second electrode disposed in position to make contact with skin in the region of the user's hand when the handheld sensor is supported thereat; and which is connected to the floormat via a cable having one or more electrical conductors disposed therein. The system also includes an analog system configured to receive biometric signals from the first electrode and from the second electrode and to process the biometric signals to generate an ECG waveform including a series of QRS complexes, with the analog system being located in either the Floormat or the Handheld Sensor and the electrode that is disposed in the other device being electrically connected to the analog system by means of the electrical conductors in the cable, as well as a processing system configured to receive the time-dependent load-cell waveform from the floormat sensor and the ECG waveform from the analog system. The processing system is further configured 1) to analyze the series of QRS complexes in the ECG waveform to determine a set of fiducial markers, and then 2) to analyze the set of fiducial markers to average together multiple sections of the time-dependent load-cell voltage waveform to determine the BCG signal from a user.

In embodiments, AC components may be isolated from the load cell waveform, and then analyzed using an ECG waveform to identify fiducial points therein. Multiple waveform segments may be averaged to form an average waveform segment, which is then processed to identify a BCG pulse from which a physiological parameter of interest may be determined. In another aspect, the invention features a sensor for determining a physiological parameter (e.g. cardiac contractility) from the BCG pulse.

In embodiments, well-defined fiducial points, such as a pulse from the ECG, PPG, IMP and/or BR waveforms, may be used to analyze the BCG signal. One or more segments of the BCG signal could then be analyzed (e.g., by averaging multiple segments) to determine a physiological parameter of interest.

In another aspect, pulsatile components from time-dependent waveforms measured by the Floormat and Handheld Sensor can be collectively analyzed to determine a pulse transit time (PTT). Such pulsations maybe be included in the ECG, PPG, TBI, BR, and/or BCG waveforms. The pulse transit time is then used to calculate a BP value.

In another aspect, the invention features a biometric sensor system having a Floormat and a Handheld Sensor generally as described above. The Floormat includes a load cell-based weight-measurement system and an electrode disposed at its upper surface to contact the sole of one of the user's feet. The Handheld Sensor also includes an electrode, which, together with the Floormat sensor, is used to generate an ECG waveform. By processing a load cell waveform generated by the load cell system and the ECG waveform, a given user using the system can be identified.

In another aspect, the invention features a biometric sensor system having a Floormat and a Handheld Sensor generally as described above. The Floormat includes a load cell-based weight-measurement system. A processing system receives and processes a time-dependent load-cell waveform to identify user stability and/or palsy. In particular, a load-cell waveform with little variation in amplitude (e.g., below a certain predetermined threshold) and/or relatively low contribution from high-frequency components (e.g., below a certain predetermined threshold) may be characterized as corresponding to a user that has acceptable balance. On the other hand, a user with balance difficulties or palsy may be identified by load-cell waveforms having a high degree of amplitude variation (e.g., as expressed in terms of amplitude variation as a percentage of a baseline or average value) or a high contribution to the waveform from high-frequency components.

The measurement system described herein has many advantages. Collectively, the Floormat and Handheld Sensor provide a single, easy-to-use system that a user can deploy to measure all their vital signs, complex hemodynamic parameters, and basic wellness-related biometric parameters such as weight, percent body fat, and muscle mass. Ideally the system is used in much the same way as a conventional bathroom scale. Such ease of use may increase compliance, thereby motivating daily use. And with this, the measurement system can calculate trends in a user's physiological parameters, thereby allowing better detection of certain disease states and/or management of chronic conditions such as HF, CHF, diabetes, hypertension, chronic obstructive pulmonary disease (COPD), ESRD, and kidney failure.

Still other advantages should be apparent from the following detailed description, and from the claims.

DETAILED DESCRIPTION

1. System Overview

Figure 1:
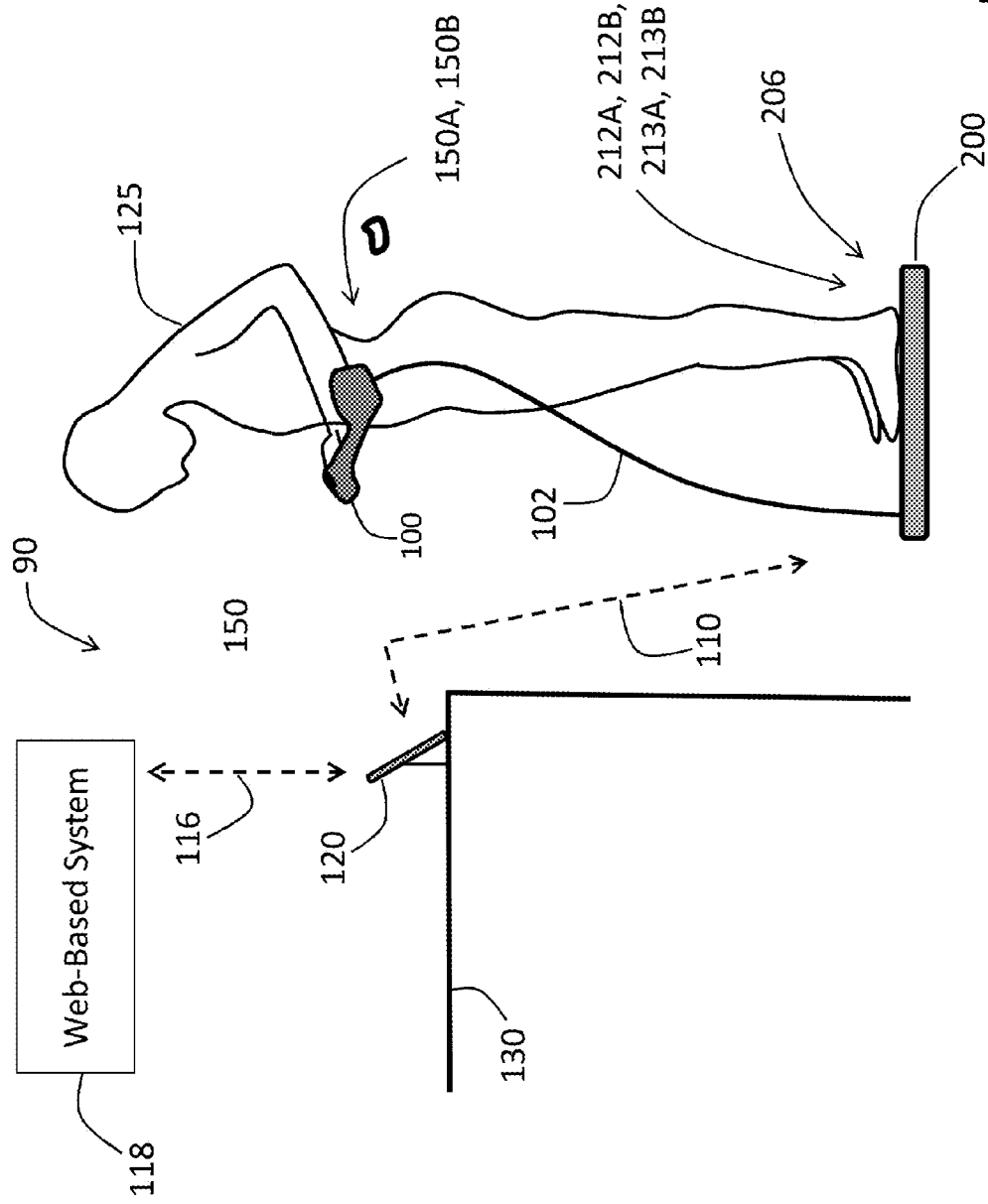
FIG. 1 is a schematic, side view of a user being monitored by the system according to the invention, which includes a Floormat that the user stands on, a cable-connected Handheld Sensor that the user holds while they stand on the Floormat, and a mobile device that connects wirelessly to the system and to a web-based system.

FIG. 1 shows a system 90 featuring a Floormat 200 and Handheld Sensor 100, electrically connected to each other by a conductor-bearing cable 102, that work in concert to measure a user 125 according to the invention. Both the Floormat 200 and Handheld Sensor 100 feature a collection of physiological sensors that connect to the user 125, as described in detail below, to measure time-dependent physiological waveforms, and from these physiological parameters. A wireless device (e.g. a Bluetooth® radio) within the Floormat 200 transmits both the waveforms and parameters to an external mobile device 120. The goal of the system 90 is to quickly and non-invasively measure all five vital signs (HR, RR, SpO2, BP, and TEMP), hemodynamic parameters (SV, CO, TFC, Fluids), and biometric parameters (weight, body composition) with a system 90 that is easy-to-use, low-cost, inconspicuous, and seamlessly connects to the cloud. A rationale for the system 90 is that most disease states are predicted not by a single parameter (e.g. BP), but rather by a collection or 'constellation' of parameters that may trend in different directions. However a complicating factor in monitoring such parameters is that they typically cannot be measured with a single device, or from a single location on the body. Thus, the system 90 is designed to measure all the above-described parameters using as few sensors as possible.

Figure 5:
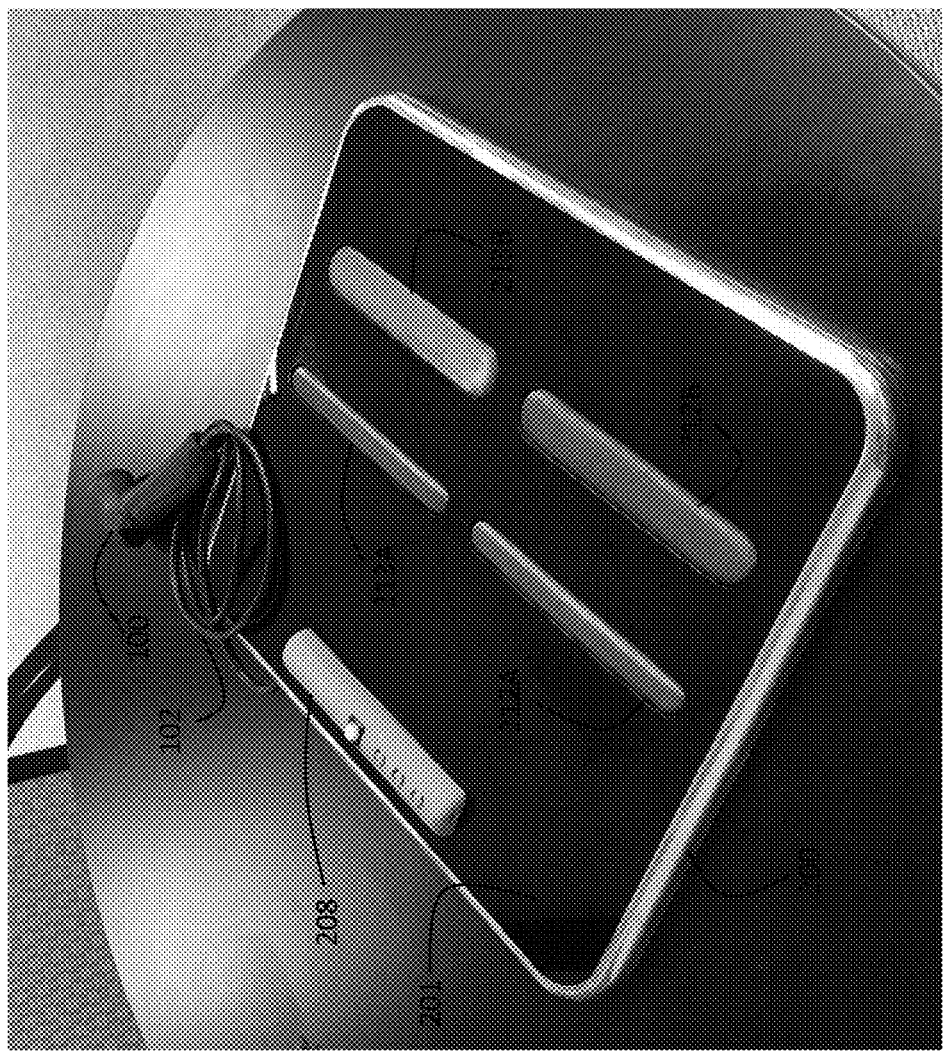
FIG. 5 is a photograph of the Floormat of FIG. 4, including a top portion to cover the internal components shown in FIG. 4.
Figure 6:
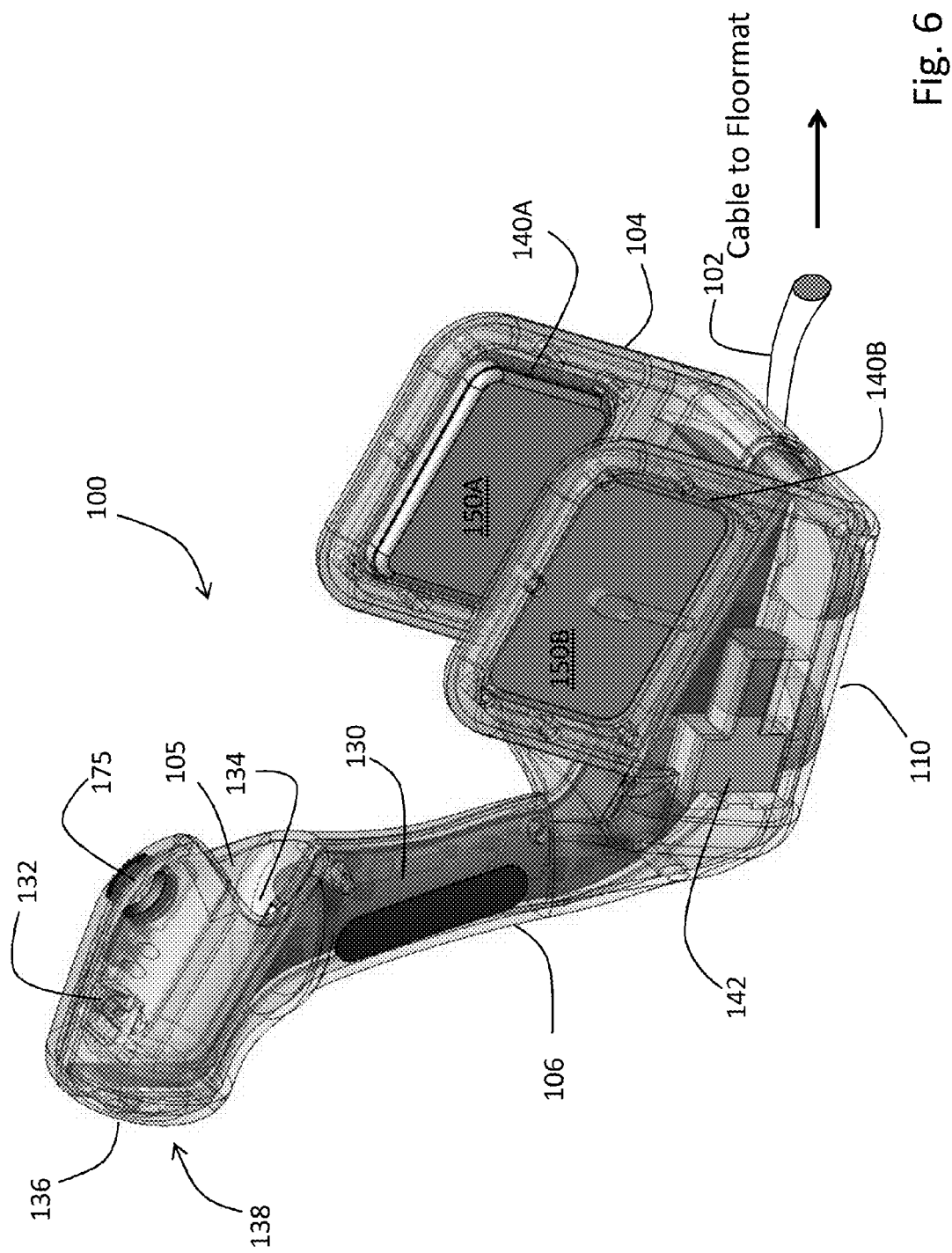
FIG. 6 is a three-dimensional, side view of the Handheld Sensor wherein the Sensor's mechanical housing is shown as being transparent to indicate the Sensor's internal components.
Figure 8B:
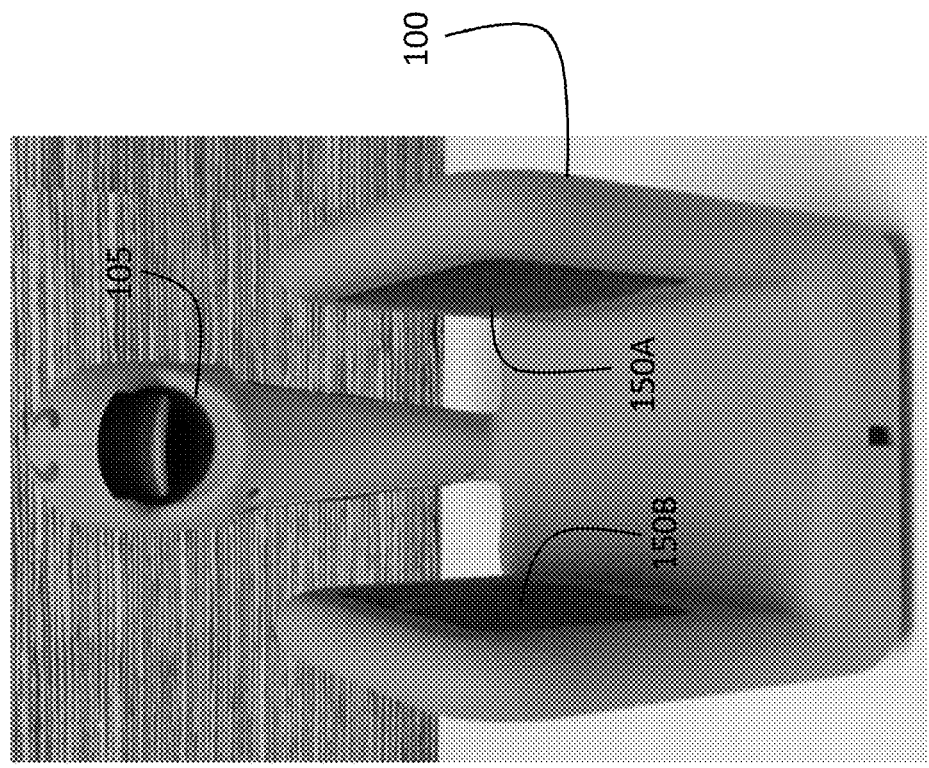
FIG. 8B is a photograph of the Handheld Sensor's electrodes shown in FIG. 8A in an un-inflated state.
Figure 8A:
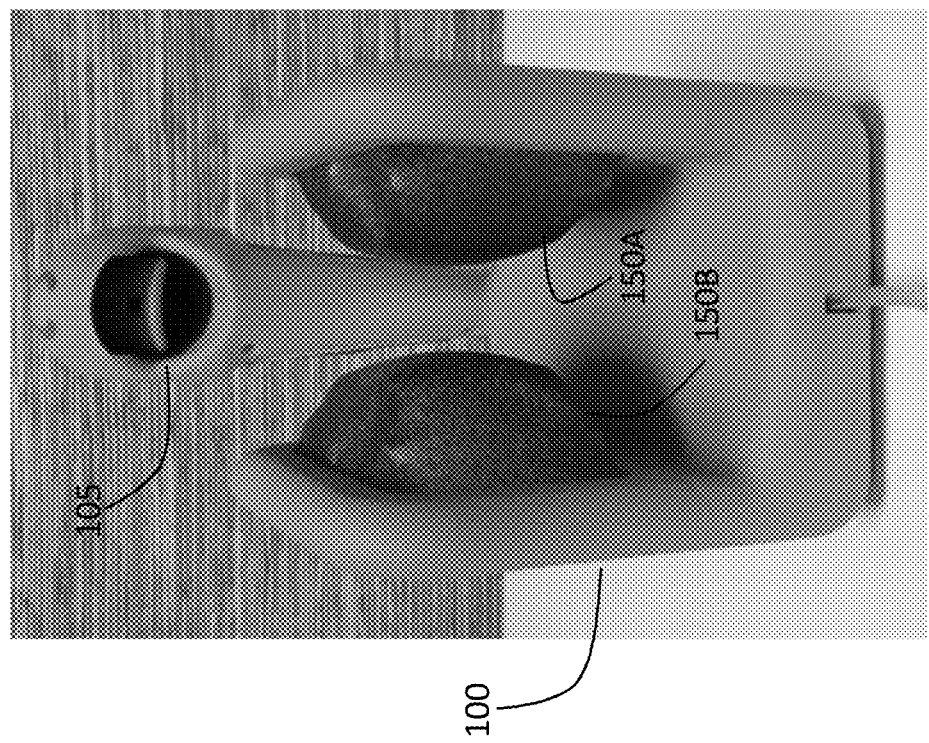
FIG. 8A is a photograph of the Handheld Sensor's electrodes, which include inflatable bladders covered with a fabric that is both stretchable and conductive, in an inflated state.

To measure ECG and TBI waveforms, the Floormat 200 includes two sets of electrodes 212A, 212B, 213A, 213B, as shown in FIGS. 1 and 5, and the Handheld Sensor 100 includes a single set of electrodes 150A, 150B, as shown in FIGS. 6, 8A, and 8B). All of the electrodes 212A, 212B, 213A, 213B, 150A, 150B may be made from a common reusable material, most preferably a stretchable conductive fabric pulled over a soft substrate such as foam, as is described in more detail below. The electrodes contact the user's skin during use, but do not adhere to it. They connect through wires (i.e., conductors) to a circuit board 206 located within the Floormat 200. Collectively the electrodes 212A, 212B, 213A, 213B, 150A, 150B establish a 'conduction pathway' over which bioelectric signals are generated, collected, and eventually processed by the circuit board 206 to measure ECG, TBI, and BR waveforms, described in more detail below. More specifically, during a measurement the electrodes 150A, 150B within the Handheld Sensor 100 inflate and contact the user's wrist. They connect to the circuit board 206 through wires in the cable 102, whereas the electrodes in the Floormat are in direct electrical contact with metal traces on the circuit board 206. (In an alternate configuration, the circuit board 206 could be located in the Handheld Sensor 100 instead of the Floormat 200; in that case, the electrodes in the Handheld Sensor 100 would be in direct electrical contact with metal traces on the circuit board 206 and the electrodes within the Floormat 200 would connect to the circuit hoard 206 via conductors in the cable 102.) One electrode 150A in the Handheld Sensor 100 injects electrical current into the user's wrist, while the other 150B senses a bioelectric signal related to the impedance (i.e. resistance) encountered by injected current. Similarly, one electrode 212A in the Floormat 200 injects a similar electrical current into sole of, for example, the user's left foot, while the other 212B senses a similar bioelectric signal.

Current injected by the two electrodes 150A, 212A is typically modulated at a relatively high frequency (e.g. 100 kHz) and low amperage (typically about 4-8 mA), and is out of phase by 180°. Both biometric signals feed into circuits (e.g., differential amplifiers) on the circuit board 206, which processes them to yield TBI waveforms featuring both AC and DC components. Further processing of the AC components yields measurements of SV, CO, and RR, while that for the DC components yields measurements of Fluids and TFC, as described in more detail below.

The same bioelectric signals collected by the electrodes 150B, 212B within, respectively, the Handheld Sensor 100 and Floormat 200 are additionally processed by systems (i.e., circuits and computer code being executed on a microprocessor) the circuit board 206 to yield an ECG waveform. With further processing (e.g. detection of R-R intervals in neighboring QRS complexes), the ECG waveform yields HR and HRV. To counteract the well-known effects of noise caused by common-mode frequencies (typically present at 50 or 60 Hz, and caused by the electrical grid), the electrode 213A contacting the user's right foot injects a low-amperage current modulated at the common-mode frequency. The injected current is typically 180° out of phase with the common-mode noise present in the unprocessed ECG waveform, and the amperage of the current is modulated according to the level of the noise. This is the well-known functionality of a 'right-leg drive' electrode and circuit. Suitably, the electrode 213B may have no function, and is simply present to add symmetry to the configuration of electrodes on the Floormat's top surface. Alternatively, the electrode 213B may be electrically connected to its neighboring electrode 212B to collect additional bioelectric signals for the ECG waveform.

With the inventive system described herein, the Floormat 200 and Handheld Sensor 100 work in concert to measure ECG, TBI, and BR waveforms as measured across the user's entire body (i.e., hand to foot), as opposed to just a relative small portion of the body (e.g., thoracic cavity) as measured by previously known systems. Such a measurement across a conduction pathway extending from the user's foot to the user's hand region is particularly advantageous for measuring TBI waveforms, which feature a DC component that is calculated over the conduction pathway and that is used to calculate TFC and Fluids. A relatively large pathway, like that measured by the combination of the Floormat and Handheld Sensor, may be more indicative of full-body impedance.

Figure 2:
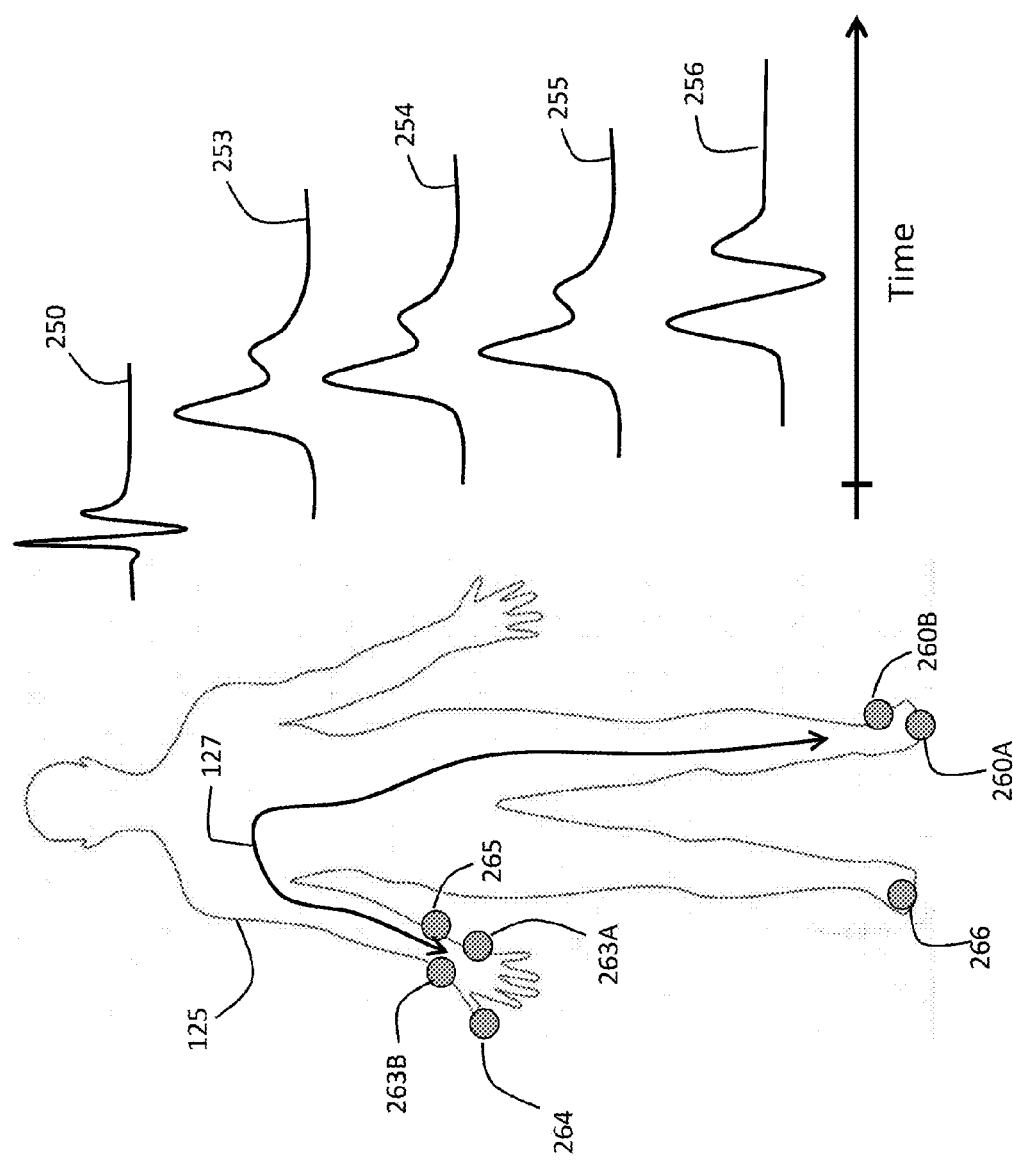
FIG. 2 is a schematic drawing showing a current conduction path and locations on the human body were the Floormat and Handheld Sensor collectively measure time-dependent, physiological waveforms from the user.

FIG. 2 shows a schematic drawing indicating how the inventive device described herein measures waveforms having pulsatile components along different portions of the user's body, with each portion separated from the source of the pulsatile components—the user's heart—by a sequentially increasing distance. More particularly, the figure shows a schematic indication of whole-body measurements made with the combined Floormat and Handheld Sensor, as described above. Here, the arrow 127 indicates the conduction pathway over which bioelectric signals are measured to generate an ECG waveform 250 and the AC component of the TBI waveform 253 (and, in embodiments, a similar component from BR waveforms, although these are not shown in the figure). The AC component of the TBI waveform 253, which is described in more detail below and referred to as $\Delta Z$, primarily indicates blood flow from the heart's left ventricle into the aorta. Electrodes in the Floormat measure these waveforms from a first distal point of the arrow 127, as indicated by circles 260A, 260B, with the two circles indicating the pair of electrodes (one for current injection; one for sensing bioelectric signals). Signals from these electrodes are combined with signals measured by the electrodes in the Handheld Sensor at the other distal point of the arrow 127, as indicated by circles 263A, 263B, to measure the ECG 250 and TBI 253 waveforms. The ECG waveform 250 features a pulsatile component, called a QRS complex, which indicates initial electrical activity in the user's heart and, informally, marks the beginning of the cardiac cycle.

Simultaneously, optics (i.e. LEDs and a photodetector) within the Handheld Sensor measure pulsatile components in the PPG waveform 254, sampled from arteries within the user's thumb as indicated by the circle 264. The PPG waveform 254 indicates a heartbeat-induced volumetric expansion in the artery lying beneath the optics. The inflatable electrodes in the Handheld Sensor, coupled with pressure-measuring electronics, sense pulsatile components from a pressure waveform 255 measured from the user's wrist as indicated by circle 265. Similar to the PPG waveform 254, the pressure waveform 255 indicates a heartbeat-induced increase in pressure, primarily in the radial and ulnar arteries. Finally, load cells in the Floormat measure BCG waveforms 256 from a slight heartbeat-induced volumetric expansion in the user's foot, as indicated by circle 266.

The Floormat 200 and Handheld Sensor 100 may each use parameters measured wholly or in part by the other device to complete their own measurement. For example, ΔZ waveforms measured as described above may use weight or an SV calibration, as measured by the Floormat 200, to determine SV. Likewise, ECG waveforms measured as described above may be used as a fiducial marker to perform a 'beatstacking' algorithm, described in more detail below, to measure BCG pulses.

Figure 3:
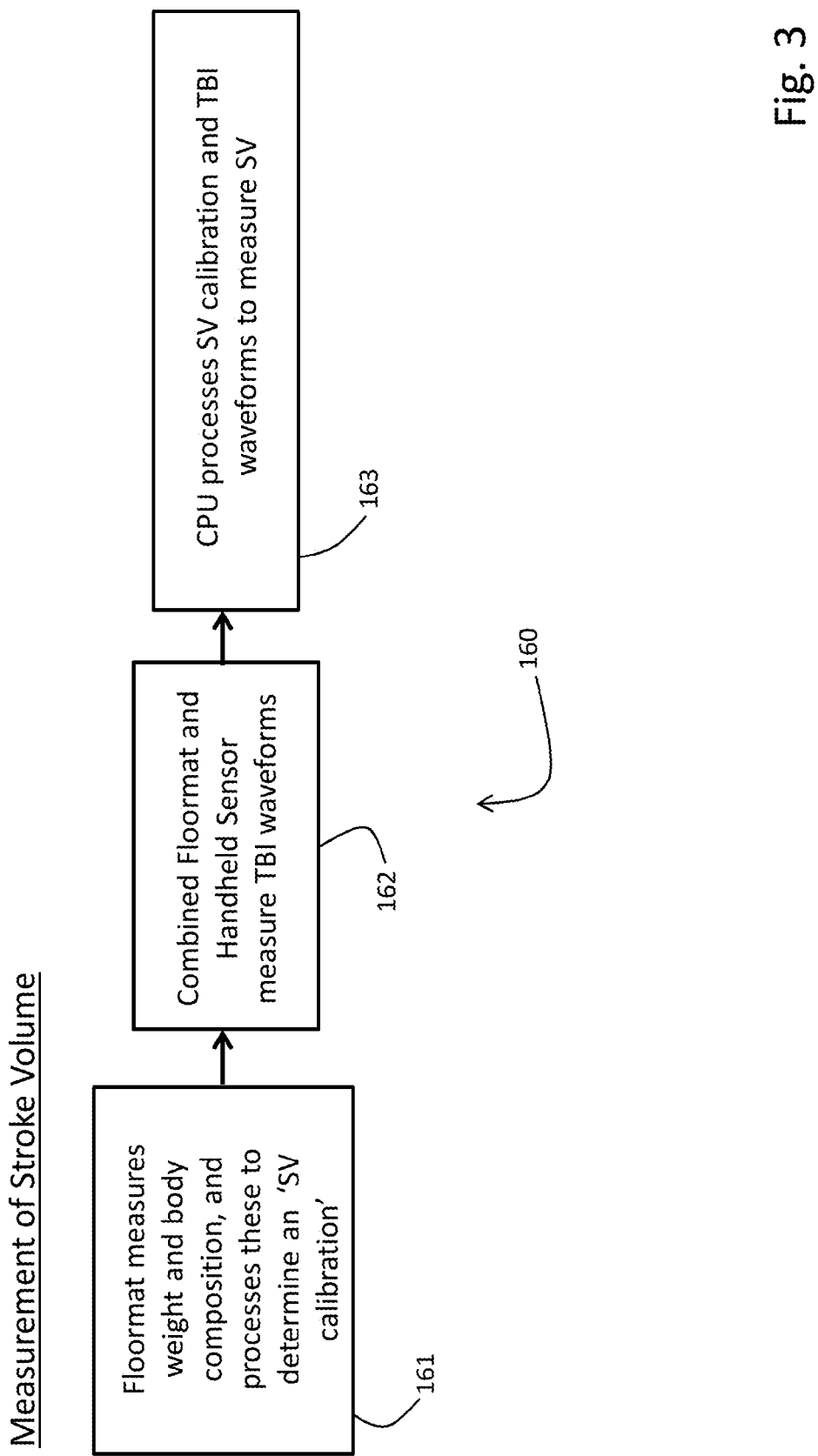
FIG. 3 is a flow chart of an algorithm that the system of FIG. 1 uses to calculate SV.

FIG. 3, as an example, indicates an algorithm 160 featuring a first step (161) wherein the Floormat 200 measures and processes weight and body composition to determine an 'SV calibration'. Using a second step (162), the Floormat and Handheld Sensor collectively measure TBI waveforms, which during a third step (163) a computer processing unit (CPU), suitably located in the Floormat, processes with the SV calibration to determine SV. The details of this algorithm are described in more detail, below.

Referring again to FIG. 1, a Bluetooth® transmitter located in the Floormat 200 transmits information, as shown by arrow 110, to the external mobile device 120. The mobile device 120, for example, can be a cellular telephone or tablet computer using a customized software application (e.g. one running on Android or iOS platforms, and downloaded from the cloud). During a measurement, the mobile device 120 is typically placed on a horizontal surface 130, such as a bathroom countertop. Once it receives information, the mobile device 120 transmits it to a Web-based System 118 for follow-on analysis, e.g. by a clinician or a data-analytics software platform.

2. Floormat

Figure 4:
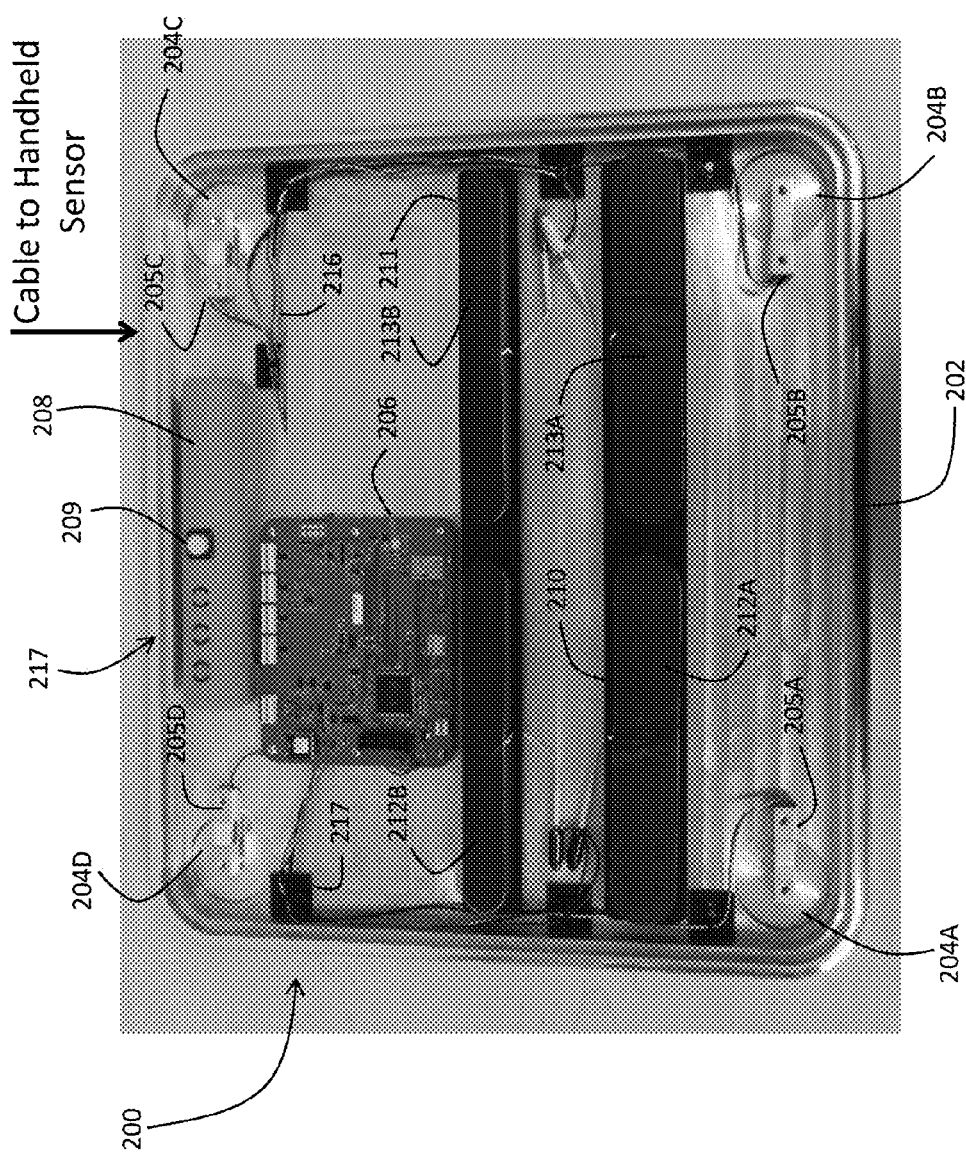
FIG. 4 is a photograph of internal components within the Floormat of FIG. 1.

FIGS. 4 and 5 show, respectively, photographs of the internal components and a top portion of a Floormat 200 according to the invention. Resembling a conventional bathroom scale that is configured to rest stably on a flat, horizontal surface, the Floormat 200 features metal base 202 that supports four load cells 205A-D, each connected to metal foot 204A-D located at a respective corner of the base 202, and a top surface 201 that houses upwardly exposed electrodes 212A, 212B, 213A, 213B for injecting current into the soles of the user's feet and sensing bioelectric signals, as described above. The metal feet 204A-D are designed to sit on a horizontal surface (e.g. a floor) to support the Floormat 200 so that the user can step onto it. During use, a voltage is applied to each load cell using a 4-wire cable 216, held in place by a plastic tab 217, which connects to the circuit board 206. (Note that each load cell connects to a unique 4-wire cable, which in turn is held in place with a unique plastic tab; only one of these components is specifically labeled/identified in the figure.) Each load cell 205A-D includes a Wheatstone Bridge (not shown in the figure), which is a 4-resistor electrical circuit featuring one or more resistors having a resistivity that varies with strain caused by an applied weight, and connects to the circuit hoard 206 with a unique 4-wire cable. A user steps on the Floormat's top surface 201 so that the soles of their feet contact each electrode 212A, 212B, 213A, 213B. Force caused by the user's weight presses down against each load cell, causing the respective Wheatstone Bridge to generate a time-dependent voltage that passes through the 4-wire cable 216 to the circuit board 206, where it is processed by separate differential amplifiers associated with each load cell to amplify the voltage resulting from the load cell's Wheatstone Bridge. The resulting voltages pass to a summing amplifier on the circuit board 206, which adds and amplifies them to generate a single voltage that is then processed by a microprocessor on the circuit board to determine the user's weight.

Additionally, high-frequency signal components from the load cells 205A-D can be further processed with the analog and digital electronics on the circuit board 206 to measure the BCG waveforms, which as described above are generated by a slight, heartbeat-induced volumetric expansion in the user's foot caused by blood ejected during systole. BCG waveforms are typically best measured using signal-processing techniques such as beatstacking, as described above. The BCG waveforms can also be collectively analyzed with ECG and/or PPG waveforms to calculate a transit time, which relates inversely to BP as described in the above-referenced patent application entitled 'FLOORMAT PHYSIOLOGICAL SENSOR', the contents of which have been incorporated herein by reference.

In certain embodiments, time-dependent voltage waveforms measured by the load cells can be used to detect parameters such as balance and even progression of diseases such as Parkinson's disease. More specifically, a user that is swaying or undergoing related motions will generate a waveform that varies in amplitude over time; this may indicate a user with 'bad' balance. Likewise, a user that stands in a stable, unwavering manner on the Floormat will generate a waveform featuring relatively stable amplitude over time, thus indicating 'good' balance. In a similar manner, a user with Parkinson's disease typically undergoes small, rapid movements or tremors that will map onto the time-dependent voltage waveform. Analysis of frequency and amplitude components within the waveforms may indicate the progression of this disease.

On its top surface 201, the Floormat 200 also includes a 'status bar' 208 that is raised relative to the top surface 201 and houses a trio of status LEDs 217 indicating the Floormat's status, along with a pushbutton on/off switch 209. The status LEDs 217 indicate, for example, if the Floormat: i) is ready for the user to step on it; ii) is making a measurement; iii) is transmitting a measurement; or iv) has completed a measurement. Other states of the Floormat, of course, can be indicated with the status LEDs 217. Each LED can emit a variety of colors and can be driven to flash at different frequencies, making it possible to indicate a large number of configurations to the user. As indicated by its name, the pushbutton on/off switch 209 turns the Floormat 200 on and off.

In a preferred embodiment, the Floormat 200 lacks a conventional display (e.g. an LCD). Instead it relies on the status LEDs to indicate the above-mentioned operation states, and displays information on the software application running on the mobile device. In alternate embodiments the Floormat may include a conventional display.

As noted above, the Handheld Sensor 100 connects to the Floormat 200 (in particular, to the circuit board 206 and the processing components contained thereon) through a flexible cable 102. The cable 102 typically includes six separate wires that connect to the circuit board and supply: i) biometric signals from electrodes for the ECG and TBI measurements; and ii) power and ground for an internal circuit board that powers the PPG and BP measurements. These components are described in more detail with reference to FIGS. 6-8.

The Floormat's top surface 201 supports sets of electrodes 212A, 212B, 213A, 213B that are secured to the metal base 202 with a pair of plastic arms 210, 211 that hold them securely in place during a measurement. Suitably, the electrodes 212A, 212B, 213A, 213B are reusable components fabricated from conductive materials such as stainless steel or foam covered with a conductive fabric. Use of other electrode materials is also within the scope of this invention.

Electrodes 212A, 212B, when combined with complementary electrodes in the Handheld Sensor 100, are used for TBI and ECG measurements, as described above. These measurements use circuitry within the circuit board 206 that features one or more differential amplifiers connected to the electrodes and which generate a time-dependent voltage. The voltage can be filtered and processed with analog circuitry to measure ECG and TBI waveforms. Measuring ECG waveforms with this technique is known in the art. To measure TBI waveforms, typically analog circuitry within the circuit board 206 separates out an AC waveform that features relatively high-frequency features ($\Delta Z(t)$), and a DC waveform that features relatively low-frequency features (this waveform is typically called $Z_0$). This technique for measuring $\Delta Z(t)$ and $Z_0$ is described in detail in the following co-pending patent applications, the contents of which have been previously incorporated herein by reference: "NECK-WORN PHYSIOLOGICAL MONITOR," U.S. Ser. No. 62/049,279, filed Sep. 11, 2014; "NECKLACE-SHAPED PHYSIOLOGICAL MONITOR," U.S. Ser. No. 14/184,616, filed Feb. 19, 2014; and "BODY-WORN SENSOR FOR CHARACTERIZING PATIENTS WITH HEART FAILURE," U.S. Ser. No. 14/145,253, filed Dec. 31, 2013; and PHYSIOLOGICAL MONITORING SYSTEM FEATURING FLOORMAT AND WIRED HANDHELD SENSOR.

For example, respiratory effort (i.e. breathing) changes the capacitance of the chest, thus imparting a series of low-frequency undulations (typically 5-30 undulations/minute) on the $\Delta Z(t)$ waveform. The Handheld Sensor's digital system processes these oscillations to determine RR.

Fluids (e.g. TFC) also conduct the injected current, and thus Fluid levels vary inversely with impedance levels: an increase in Fluid level decreases impedance, while a decrease in Fluid level increases impedance. Thus, fluids that accumulate in the thoracic cavity affect the impedance within the conduction pathway in a low-frequency (i.e. slowly changing) manner, and can be detected by processing the $Z_0$ waveform. Typically, the $Z_0$ waveform features an average value of between about 10-30 Ohms, with 10 Ohms indicating relatively low impedance and thus high fluid content (e.g. the user is 'wet'), and 30 Ohms indicating a relatively high impedance and thus low fluid content (e.g. the user is 'dry'). Time-dependent changes in the average value of $Z_0$ can indicate that the user's fluid level is either increasing or decreasing. An increase in fluid level, for example, may indicate the onset of CHF.

With calibration, the $Z_0$ waveform yields Fluid levels and changes therein, as concentrated in the user's lower extremities. Typically, changes in impedance parameters, which in turn indicate a corresponding change in Fluid level, are more relevant than absolute impedance levels.

A similar approach is used for bio-reactance and BR waveforms. However in this case, circuitry measures changes in phase corresponding to the injected current, as opposed to changes in amplitude used for bio-impedance. During a measurement, the phase difference between the injected currents and the detected currents is measured by the bio-reactance circuit and ultimately processed with the digital system on the circuit board to generate the BR waveform. The difference in phase is due to the current being slowed down by the capacitive properties of cell membranes within the conduction pathway. The baseline phase difference ($\Phi a$) is estimated from the DC component of the BR waveform. $\Phi a$ is used to calculate tissue composition, described in more detail below. The AC component of the waveform can be used to track RR, SV, and CO as described above.

Bio-reactance, when combined with bio-impedance, can measure physiological parameters related to body composition (e.g. fat, muscle, and fluid in the user's body) and the progression of disease states. These parameters, like weight, may also be used to calibrate the SV measurement. Typically, such a calibration is determined by conducting a large-scale clinical study using a known reference for SV and CO. More specifically, bio-impedance and bio-reactance measurements analyze the resistance and reactance of the user's tissue—along with biometric parameters such as height, weight and age—to generate accurate estimates of the composition of the tissue in the abdomen, chest, and arm. Such parameters may correlate with the size of the user's left ventricle and aorta, and can thus be used within $V_c$. Height, weight, and age, for example, can be input to the software application operating on the user's mobile device, and wirelessly transmitted to the Handheld Sensor for follow-on analysis (e.g., to calculate $V_c$).

Figure 7:
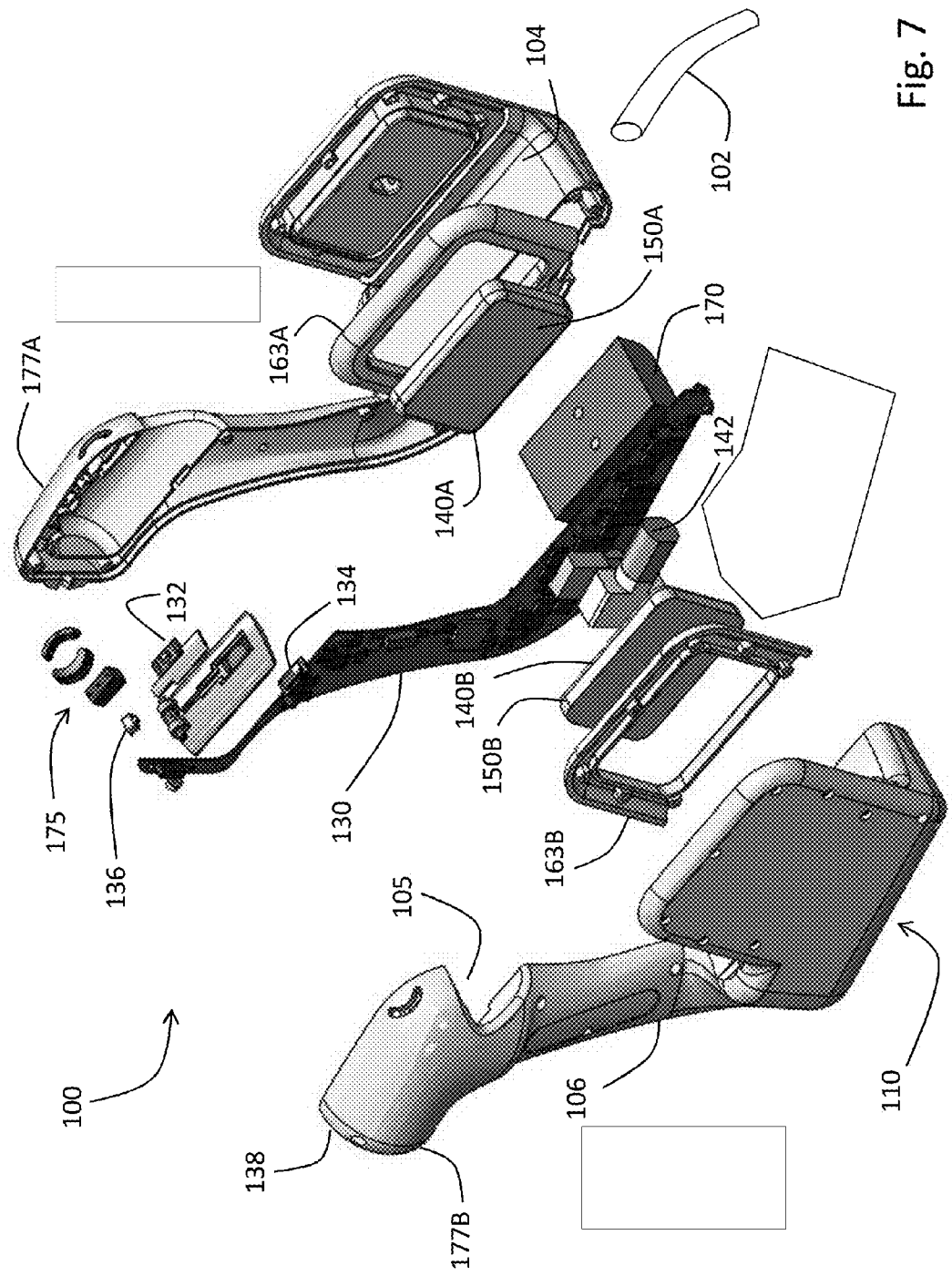
FIG. 7 is a three-dimensional, exploded view of the Handheld Sensor and its internal components.

$\Phi a$ and $Z_0$ are then used to calculate the resistance ($Z_0 \cos(\Phi a)$) and the reactance ($Z_0 \sin(\Phi a)$) of the tissue in the abdomen, chest, and right arm. Resistance and reactance have been shown to be predictive of tissue composition. For example, fatty tissue is far more electrically conductive than fat-free tissue. Therefore, a tissue's resistance is largely governed by the mass of the fat-free tissue present. This makes the inverse of a tissue's resistance a good estimator of that tissue's fat-free mass. Similarly, cell membranes have capacitive properties that cause phase changes in current that passes through the body. The greater the concentration of cells in the tissue, the greater the change in phase. When coupled with resistance, reactance can thus distinguish changes in fat from changes in fluid due to the differences in the cellularity of fat and extracellular fluid. Specifically, it has been shown that resistance and reactance—coupled with height, weight and age—can predict fat-free mass and body-fat mass as accurately as the "gold-standard" method—air displacement plethysmography. This is described in the following journal article, the contents of which are incorporated herein by reference: *Body fat measurement by bioelectrical impedance and air displacement plethysmography: a cross-validation study to design bioelectrical impedance equations in Mexican adults*; Nutrition Journal; 6: (2007). When fat-free mass, body-fat mass, and weight are measured, the root cause of changes in weight can be identified. Changes in fluid retention can signal the onset or reoccurrence of numerous medical conditions, such as CHF and ESRD. By measuring both reactance and resistance, both the Floormat and Handheld Sensor can distinguish changes in fluid retention from changes in tissue mass. This enables reliable tracking of this important parameter at home, on a daily basis. It also may improve the calculated accuracy of $V_c$, thereby improving the accuracy in calculating SV and CO 3. Handheld Sensor The Handheld Sensor 100 works in concert with the Floormat 200 and mobile device 125, as described above. FIGS. 6-8 illustrate the Handheld Sensor's measurement electronics and internal components in more detail. In general, a housing of the Handheld Sensor 100 is constructed from two generally symmetric, right and left halves 177A, 177B, which are joined together along a longitudinal midline. The housing halves 177A, 177B are suitably formed (e.g., injection molded) from a rigid material, e.g., medicalgrade plastic. A circuit board 130 is housed within an internal space formed by the right and left halves 177A, 177B of the Handheld Sensor's housing, primarily within the neck 106, and supports the electronics that drive each measurement. A battery pack 170, including two rechargeable lithium-ion batteries, powers the system. The batteries can be recharged through a standard USB connector (not shown in the figure) that connects through a cable to an AC/DC adaptor plugged into a wall outlet or, depending on power requirements, a USB port of a personal computer.

The upper portion of the circuit board 130 extends to within the cavity portion 105 and includes a dual-emitting LED 132, which generates red and infrared optical wavelengths in the 660 nm and 908 nm region, and a photodetector (e.g., photodiode) 134. These components measure PPG waveforms using both red and infrared radiation, as is generally known in the art, but quite advantageously from one of the digits (e.g., the thumb) of the hand with which the user holds the Handheld Sensor. This makes for a highly compact, easy-to-use, comprehensive device. A digital system (i.e., microprocessor featuring suitably configured computer code) within the circuit board 130 processes the waveforms to determine SpO2. Generally speaking, such measurement is described in more detail in the following co-pending patent applications, the contents of which are incorporated herein by reference: "NECK-WORN PHYSIOLOGICAL MONITOR," U.S. Ser. No. 62/049,279, filed Sep. 11, 2014; "NECKLACE-SHAPED PHYSIOLOGICAL MONITOR," U.S. Ser. No. 14/184,616, filed Feb. 19, 2014; and "BODY-WORN SENSOR FOR CHARACTERIZING PATIENTS WITH HEART FAILURE," U.S. Ser. No. 14/145,253, filed Dec. 31, 2013; and PHYSIOLOGICAL MONITORING SYSTEM FEATURING FLOORMAT AND WIRED HANDHELD SENSOR. In general and as explained in greater detail in these incorporated references, during an SpO2 measurement, the digital system alternately powers red and infrared LEDs within the dual-emitting LED 132. This process generates two distinct PPG waveforms. Using both digital and analog filters, the digital system extracts AC and DC components from the red (RED(AC) and RED(DC)) and infrared (IR(AC) and IR(DC)) PPG waveforms, which the digital system then processes to determine SpO2, as described in the above-referenced patent applications.

To measure TEMP, the Handheld Sensor 100 includes an infrared temperature sensor 136, which is mounted to an upper, forward-most portion of the circuit board 130. The infrared temperature sensor detects temperature "looking outwardly" from an upper, outer, forward-facing "nose" portion 138 of the cavity portion 105. More specifically, to measure TEMP, the Handheld Sensor 100 is held close to the user's ear (or forehead) so that the outer portion 138 is adjacent to or pressed up against either the left or right ear (or to the forehead). Because the temperature sensor is positioned where it is, the user can take a temperature reading with the same device used to measure the other physiological parameters, and without even having to remove the device from his or her hand to do so. In this configuration, the infrared temperature sensor 136 detects infrared radiation (e.g. blackbody radiation) emitted from inside the ear (or forehead), which it then converts to a temperature value using techniques known in the art. Suitably, the temperature sensor 136 is a fully digital system, meaning it receives the infrared radiation with an internal photodetector and, using an internal digital system, converts this to a temperature value that it sends through a serial interface (e.g. one based on a conventional UART or I2C interface) for follow-on processing.

A multi-color status LED assembly 175 indicates when the device turns on, a measurement is being taken, a measurement is complete, and data are being transmitted (e.g., via the cable 102). The multi-color status LED assembly 175 can change color and blink at different frequencies to indicate these states.

The generally C-shaped or U-shaped, wrist-receiving portion 104 is configured to measure physiological parameters using two complementary measurement modalities. According to one modality, the C-shaped portion measures BP, e.g. SYS, DIA, and MAP, by direct sensing of pressure. To that end, the wrist-receiving portion 104 includes a pair of inflatable/deflatable, elastomeric bladders 140A,B, which are mounted on or supported by the two generally parallel, spaced-apart walls or wings 101*a*, 101*b* that extend from the base 101*c* of the wrist-receiving portion 104; the walls form a space or opening in which the user's wrist is received. (Other shapes of the bladder-supporting walls are also acceptable. For example, even a completely circular, wrist-surrounding ring-shaped structure through which the user would insert their arm could be provided.) The bladders 140A,B are configured and arranged to inflate inwardly, i.e., into the wrist-receiving space or opening, as illustrated in FIGS. 8A and 8B. A pair of plastic supports 163A, 163B hold the inflatable bladders 140A,B in place on their respective walls. Additionally, the plastic supports 163A, 163B clamp down on stretchable cloth electrodes 150A,B, addressed below, which overlie the bladders.

A small pneumatic pump system 142, controlled by the digital system on the circuit board 130, inflates the bladders 140A,B to measure BP. In general, such pump systems are known in the art for use in connection with blood-pressure monitors such as those typically sold for home use. The pump system 142 includes a diaphragm pump; a solenoid-controlled valve to maintain or release pressure within the bladders; and suitable airline tubing leading into the bladders. Alternatively, to reduce the weight and/or size of the Handheld Sensor 100, the pneumatic pump and valves could, instead, be located in the Floormat 200 and provide air to the inflatable bladders via a tube extending from the Floormat 200 to the Handheld Sensor 100, preferably along the cable 102.

Gradual inflation of the bladders 140A,B slowly compresses the user's radial artery. As it compresses, heartbeat-induced blood-flow within the artery generates slight pressure pulsations. These create a small pressure increase in the bladders that are detected by a pressure-measuring system (not shown in the figure) within the circuit board 130 (or circuit board 206 if the pump is located in the Floormat 200), as known in the art. This yields a pressure waveform that features amplitudes of the pressure pulsations plotted against the pressure applied by the inflatable bladders 140A,B. The pressure waveform typically features a bell-shaped curve when the amplitude of each pressure pulsation is plotted against the pressure applied. The appropriate digital system processes the bell-shaped curve to determine blood pressure according to the well-known technique of oscillometry. Such a technique is described in detail in the following co-pending patent applications, the contents of which have been previously incorporated herein by reference: "NECK-WORN PHYSIOLOGICAL MONITOR," U.S. Ser. No. 62/049,279, filed Sep. 11, 2014; "NECKLACE-SHAPED PHYSIOLOGICAL MONITOR," U.S. Ser. No. 14/184,616, filed Feb. 19, 2014; and "BODY-WORN SENSOR FOR CHARACTERIZING PATIENTS WITH HEART FAIL- URE," U.S. Ser. No. 14/145,253, filed Dec. 31, 2013 and PHYSIOLOGICAL MONITORING SYSTEM FEATURING FLOORMAT AND WIRED HANDHELD SENSOR. To summarize, MAP corresponds to the applied pressure that yields the maximum amplitude of the bell-shaped curve. SYS and DIA are determined, respectively, from applied pressures that yield well-defined amplitudes on the high-pressure and low-pressure sides of MAP. More specifically, SYS typically corresponds to the applied pressure that yields a pulse amplitude on the high-pressure side of MAP that, when divided by the pulse amplitude corresponding to MAP, has a ratio of about 0.4. DIA typically corresponds to the applied pressure that yields a pulse amplitude on the low-pressure side of MAP that, when divided by the pulse amplitude corresponding to MAP, has a ratio of 0.6. Other ratios can also be used to calculate SYS and DIA according to oscillometry.

During inflation, patches of conductive fabric disposed on the outer, wrist-contacting surface of the bladders 140A,B detect biometric signals. These signals are transmitted along the conductors within the cable 102 and are processed by analog circuitry associated on the Floormat's circuit board 206 to generate ECG and TBI waveforms, as described in more detail above.

The Handheld Sensor 100 can also measure blood pressure according to an alternative direct-pressure-based technique. This technique involves monitoring PPG waveforms generated by the SpO2 measuring system (i.e., by either red or infrared wavelengths emitted by the dual-emitting LED 132 and detected by the photodetector 134) while the inflatable bladders 140A,B apply pressure to the user's radial artery. Here, the applied pressure slowly reduces blood flow through the artery, causing heartbeat-induced PPG-waveform pulsations (i.e. pulsations in the RED(AC) or IR(AC) components of the PPG waveforms) to slowly increase, and then gradually decrease. As with oscillometry, the maximum amplitude of the pulsations typically corresponds to an applied pressure equal to MAP. The pulsations are completely eliminated when the applied pressure is equal to SYS, since at this pressure the radial artery is fully occluded, thus ceasing all blood flow. DIA can be determined from MAP and SYS using equations described in the above-referenced patent applications, the contents of which have been previously incorporated herein by reference.

Believed to be unique to the Handheld Sensor 100, the wrist-contacting electrodes 150A, 150B are coincident with (i.e., overlie) the inflatable bladders 140A, 140B, respectively, such that the overall system includes what are effectively inflatable electrodes. As a result, when the bladders are inflated in connection with measuring BP via direct, mechanical measurement of pressure, the electrodes are pressed firmly against the user's skin, thereby enhancing electrical contact and accuracy/reliability of the electrophysiological measurements being taken. Additionally, such an arrangement facilitates the compact, self-contained form factor of the Handheld Sensor 100.

To this end, and as shown in more detail in FIGS. 8A and 8B, the electrodes 150A, 150B are formed from a stretchable, conductive fabric that is stretched over the inflatable bladders. In general, the electrode material is conductive fabric that has conductive elements interwoven in an elastic material. Resistivity is essentially 0 Ohms in both stretched and unstretched configurations. Suitably, the fabric is able to stretch by at least 25% along at least one dimension when the inflatable bladder is inflated, and preferably it is able to stretch by roughly 50% of its original dimension when force is applied to it.

Both the Floormat and the Handheld Sensor may include a vibrating component to indicate when a measurement is complete. These systems may also include accelerometers to detect motion of the user. This information can be used, for example, to improve measurement quality by selectively detecting an ideal measurement period when motion is minimized. Accelerometers can also be used to detect the user's motion and thus initiate specific measurements, such as measurement of TEMP as described above, and also measurements performed by the Floormat. This approach, for example, would obviate the need for the pushbutton on/off switch (component 209 in FIG. 4) described above.

4. Other Measurements—Pulse Transit Time

The detection and analysis of each of the above-described physiological waveforms indicates blood flow through the user's body. More specifically, the circuitry can analyze the pulsatile components to determine parameters such as PTT, pulse arrival time (PAT), and vascular transit time (VTT). Such transit times can be used, for example, to calculate blood pressure, e.g. SYS, DIA, and MAP. This methodology is described in more detail in the following co-pending patent applications, the contents of which have been previously incorporated herein by reference: "NECK-WORN PHYSIOLOGICAL MONITOR," U.S. Ser. No. 62/049,279, filed Sep. 11, 2014; "NECKLACE-SHAPED PHYSIOLOGICAL MONITOR," U.S. Ser. No. 14/184,616, filed Feb. 19, 2014; and "BODY-WORN SENSOR FOR CHARACTERIZING PATIENTS WITH HEART FAILURE," U.S. Ser. No. 14/145,253, filed Dec. 31, 2013 and PHYSIOLOGICAL MONITORING SYSTEM FEATURING FLOORMAT AND WIRED HANDHELD SENSOR.

Figure 9:
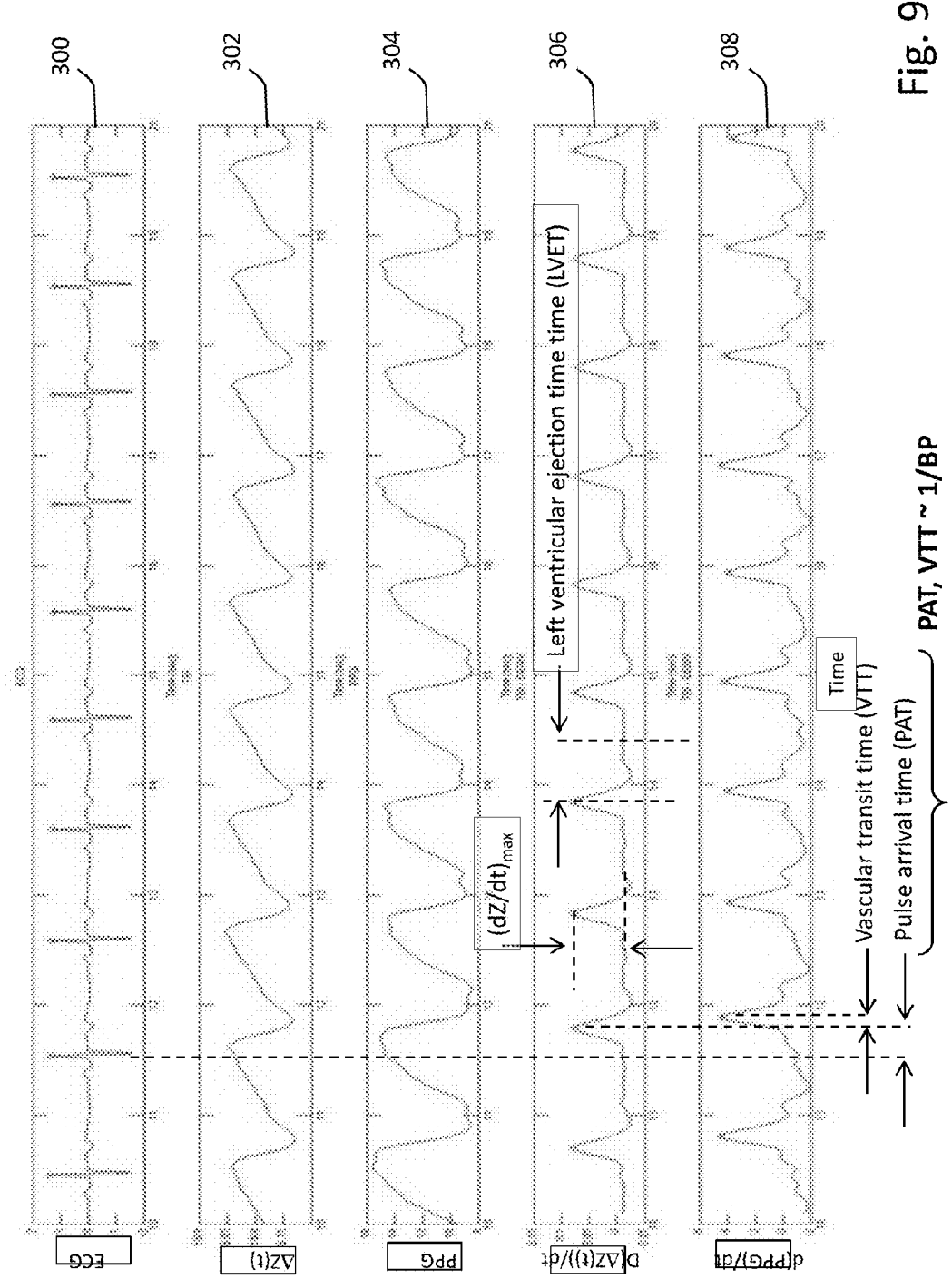
FIG. 9 is a plot of time-dependent ECG, $\Delta Z(t)$, PPG, $d(\Delta Z(t))/dt$, and $d(PPG)/dt$ waveforms measured via the Handheld Sensor and the Floormat.

To summarize, FIG. 9 shows the following time-dependent waveforms, as measured by the Floormat and/or Handheld Sensor: ECG (plot 300), $\Delta Z(t)$ (plot 302), PPG (plot 304), $d(\Delta Z(t))/dt$ (plot 306), and $d(PPG)/dt$ (plot 308). As shown in plots 300 and 302, individual heartbeats produce time-dependent pulses in both the ECG and $\Delta Z(t)$ waveforms. As is clear from the data, pulses in the ECG waveform precede those in the $\Delta Z(t)$ waveform. The ECG pulses—each featuring a sharp, rapidly rising QRS complex—mark the beginning of the cardiac cycle.

$\Delta Z(t)$ pulses follow the QRS complex by about 100 ms and indicate blood flow through arteries in the region of the body where the cloth electrodes make contact with the skin. During a heartbeat, blood flows from the user's left ventricle into the aorta; the volume of blood that leaves the ventricle is the SV. Blood flow periodically enlarges this vessel, which is typically very flexible, and also temporarily aligns blood cells (called erythrocytes) from their normally random orientation. Both the temporary enlargement of the vessel and alignment of the erythrocytes improves blood-based electrical conduction, thus decreasing the electrical impedance as measured with $\Delta Z(t)$. The $d(\Delta Z(t))/dt$ waveform (plot 306) shown in FIG. 9 is a first mathematical derivative of the raw $\Delta Z(t)$ waveform, meaning its peak represents the point of maximum impedance change.

A variety of time-dependent parameters can be extracted from the ECG and TBI waveforms. For example, as noted above, it is well know that HR can be determined from the time separating neighboring ECG QRS complexes. Likewise, left ventricular ejection time (LVET) can be measured directly from the derivative of pulses within the $\Delta Z(t)$ waveform, and is determined from the onset of the derivatized pulse to the first positive-going zero crossing. Also measured from the derivatized pulses in the $\Delta Z(t)$ waveform is $(d\Delta Z(t)/dt)_{max}$, which is a parameter used to calculate SV as described above.

The time difference between the ECG QRS complex and the peak of the derivatized ΔZ(t)waveform represents a pulse arrival time PAT, as indicated in FIG. 9. This value can be calculated from other fiducial points, including, in particular, locations on the ΔZ(t) waveform such as the base, midway point, or maximum of the heartbeat-induced pulse. Typically, the maximum of the derivatized waveform is used to calculate PAT, as it is relatively easy to develop a software beat-picking algorithm that finds this fiducial point.

PAT correlates inversely to SYS, DIA, and MAP, which can be calculated as described in the above-referenced patent applications using user-specific slopes for SYS and DIA, measured during a calibration measurement. (Such a measurement can, for example, be performed with the inflatable bladders and optical systems described above.) Without the calibration, PAT only indicates relative changes in SYS, DIA, and MAP. The calibration yields both the user's immediate values of these parameters. Multiple values of PAT and blood pressure can be collected and analyzed to determine user-specific slopes, which relate changes in PAT with changes in SYS, DIA, and MAP. The user-specific slopes can also be determined using pre-determined values from a clinical study, and then combining these measurements with biometric parameters (e.g. age, gender, height, weight) collected during the clinical study.

In embodiments of the Handheld Sensor, waveforms like those shown in FIG. 9 can be processed to determine transit times such as PAT and VTT. The Floormat and/or Handheld Sensor can use these parameters, combined with a calibration determined as described above, to calculate blood pressure without a mechanism that applies pressure, e.g. the inflatable bladders described above. Typically PAT and SYS correlate better than PAT and DIA.

PP can be used to calculate DIA from SYS, and can be estimated from either the absolute value of SV, SV modified by another property (e.g. LVET), or the change in SV. In the first method, a simple linear model is used to process SV (or, alternatively, SV×LVET) and convert it into PP. The model uses the instant values of PP and SV, determined as described above from a calibration measurement, along with a slope that relates PP and SV (or SV×LVET) to each other. The slope can be estimated from a universal model that, in turn, is determined using a population study.

Alternatively, a slope tailored to the individual user can be used. Such a slope can be selected, for example, using biometric parameters characterizing the user as described above.

Here, PP/SV slopes corresponding to such biometric parameters are determined from a large population study and then stored in computer memory on the Floormat and/or Handheld Sensor. When a device is assigned to a user, their biometric data is entered into the system, e.g. using a GUI operating on a mobile device, that transmits the data to the Floormat and/or Handheld Sensor via Bluetooth®. Then, an algorithm processes the data and selects a user-specific slope. Calculation of PP from SV is explained in the following reference, the contents of which are incorporated herein by reference: "*Pressure-Flow Studies in Man. An Evaluation of the Duration of the Phases of Systole,*" Harley et al., *Journal of Clinical Investigation*, Vol. 48, p. 895-905, 1969. As explained in this reference, the relationship between PP and SV for a given user typically has a correlation coefficient r that is greater than 0.9, which indicates excellent agreement between these two properties. Similarly, in the above-mentioned reference, SV is shown to correlate with the product of PP and LVET, with most users showing an r value of greater than 0.93 and the pooled correlation value (i.e., the correlation value for all subjects) being 0.77. This last value indicates that a single linear relationship between PP, SV, and LVET may hold for all users.

More preferably, PP is determined from SV using relative changes in these values. Typically, the relationship between the change in SV and change in PP is relatively constant across all subjects. Thus, similar to the case for PP, SV, and LVET, a single, linear relationship can be used to relate changes in SV and changes in PP. Such a relationship is described in the following reference, the contents of which are incorporated herein by reference: "*Pulse pressure variation and stroke volume variation during increased intra-abdominal pressure: an experimental study,*" Didier et al., *Critical Care*, Vol. 15:R33, p. 1-9, 2011. Here, the relationship between PP variation and SV variation for 67 subjects displayed a linear correlation of r=0.93, which is an extremely high value for pooled results that indicates a single, linear relationship may hold for all users.

From such a relationship, PP can be determined from the impedance-based SV measurement, and SYS can be determined from PAT. DIA can then be calculated from SYS and PP.

Another parameter, VTT, can be determined from pulsatile components in the ΔZ(t) (or d(ΔZ(t))/dt) waveform and the PPG (or d(PPG)/dt) waveform. FIG. 9 shows in more detail how VTT is determined. It can be used in place of PAT to determine blood pressure, as described above. Using VTT instead of PAT in this capacity offers certain advantages, namely, lack of signal artifacts such as pre-injection period (PEP) and isovolumic contraction time (ICT), which contribute components to the PAT value but which are not necessarily sensitive to or indicative of blood pressure.

Alternatively, the pulsations in the BCG waveform can be processed as described above to calculate PTT, PAT, and/or VTT.

In general, the overarching purpose of a system that combines the Floormat and Handheld Sensor according to the invention, as described above, is to make daily measurements of a wide range of physiological parameters that, in turn, can be analyzed to diagnose specific disease states. Use of a single system, as opposed to multiple devices, can simplify operation and reduce the time required to measure the above-mentioned parameters. This, in turn, may increase the user's compliance, as it is well established that daily use of devices that measure physiological parameters typically improves as the time and complexity required for such devices decreases.

By consistently collecting physiological information on a daily basis, the combined Floormat and Handheld Sensor can calculate trends in the information. Such trends may indicate the progression of certain disease states in a manner that is improved relative to one-time measurements of certain parameters. For example, a value of fluids corresponding to 15 Ohms, or an SV corresponding to 75 mL, has little value taken in isolation. But if these parameters decrease by 20% over a period of a few days, it can indicate that the user's heart is pumping blood in a less efficient manner (as indicated by the SV), which in turn decreases perfusion of their kidneys and causes them to retain more fluids (as indicated by the fluid level).

Figure 10:
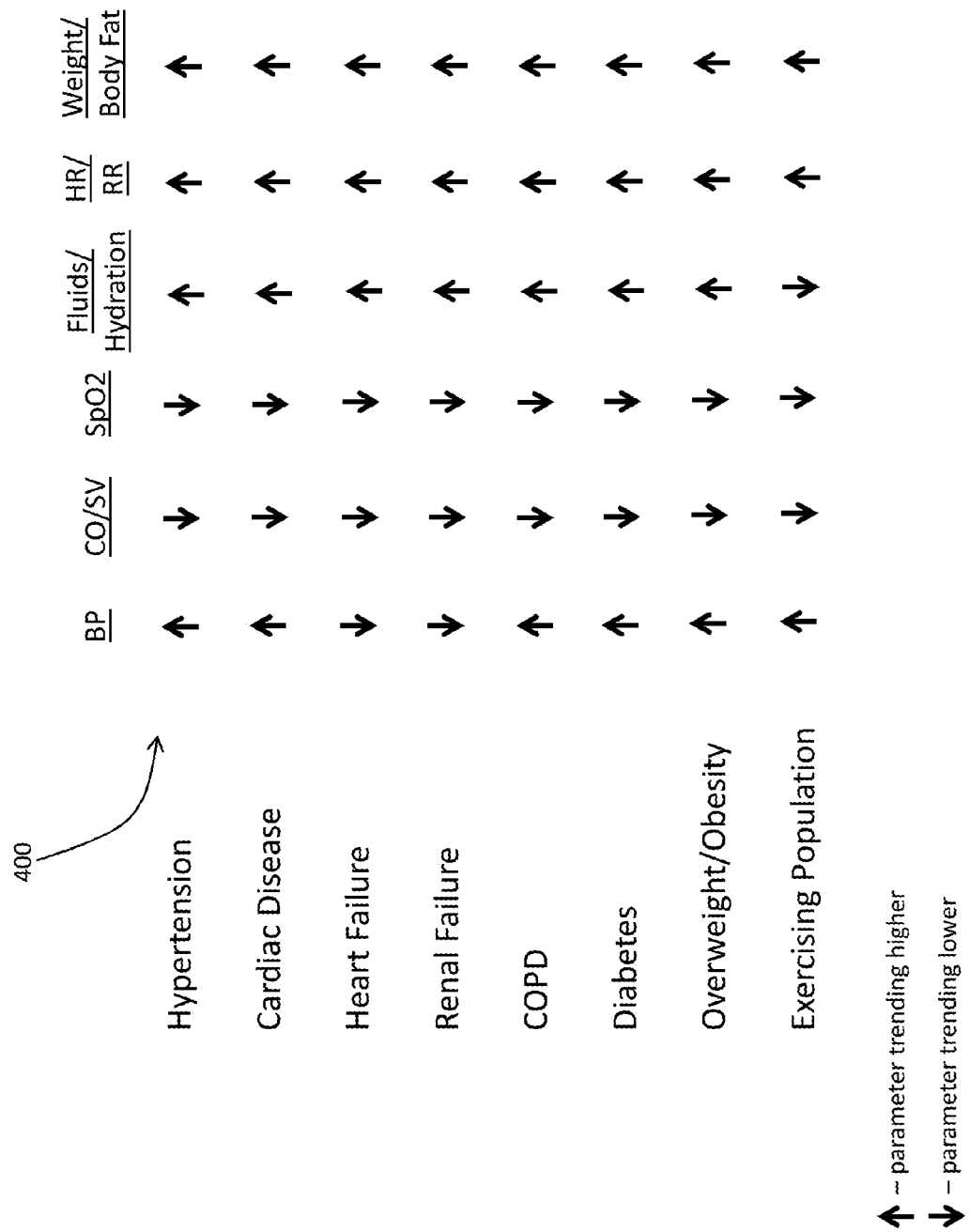
FIG. 10 is a table showing various physiological conditions and how they are predicted by trends in certain physiological parameters measured by the system of FIG. 1.

In this regard, FIG. 10 shows, for example, a table 400 indicating how trends in different physiological parameters can be used to diagnose disease states such as hypertension, cardiac disease, HF (including CHF), renal failure (including ESRD), COPD, diabetes, and obesity. In addition, the table 400 indicates how such trends may show beneficial progress to a population actively involved in exercise.

Still other embodiments are within the scope of the invention. For example, both the Handheld Sensor and Floormat can take on mechanical configurations that are different than those shown in FIGS. 1 and 4-8. For example, the flexible cable that connects the Floormat and Handheld Sensor may be replaced by a rigid component, such as a vertical plastic component that encloses the cable. The vertical plastic component may include handles that include the electrodes. The Handheld Sensor may be replaced by a patch or similar component, including both optics and electrodes, which attaches to the user's chest, as opposed to being held in the user's hand. The electrodes in the Handheld Sensor may be exclusively in the Sensor's grip and not disposed on top of the inflatable bladders, as is the case of the Handheld Sensor shown in FIG. 5. With such a configuration, BP would be determined strictly by processing PTT, PAT, and/or VTT as described above. Here, electrodes may be fabricated from either disposable or reusable components. Likewise, the Handheld Sensor, and not the Floormat, may include an electrode used for the right leg drive circuit. The Floormat may also include a mechanical, optical, or electrical mechanism configured to measure the user's height. Algorithms that process time-dependent physiological waveforms, such as ECG, TBI, PPG, BR, BCG, and pressure waveforms, may be different than those described herein, granted they perform a similar function of calculating a physiological parameter, e.g. a vital sign or hemodynamic parameter. Likewise, a pulse transit time, such as a PAT or VTT, can be calculated from one or more pulsatile components selected from one or more of the time-dependent physiological waveforms described herein.

In other embodiments, the Floormat described above can integrate with a 'patch' that directly adheres to a portion of a patient's body, or a 'necklace' that drapes around the patient's neck. The patch would be similar in form to the necklace's base, although it may take on other shapes and form factors. It would include most or all of the same sensors (e.g. sensors for measuring ECG, TBI, and PPG waveforms) and computing systems (e.g. microprocessors operating algorithms for processing these waveforms to determine parameters such as HR, HRV, RR, BP, SpO2, TEMP, CO, SV, fluids) as the base of the necklace. However unlike the system described above, the battery to power the patch would be located in or proximal to the base, as opposed to the strands in the case of the necklace. Also, in embodiments, the patch would include a mechanism such as a button or tab functioning as an on/off switch. Alternatively, the patch would power on when sensors therein (e.g. ECG or temperature sensors) detect that it is attached to a patient.

In typical embodiments, the patch includes a reusable electronics module (shaped, e.g., like the base of the necklace) that snaps into a disposable component that includes electrodes similar to those described above. The patch may also include openings for optical and temperature sensors as described above. In embodiments, for example, the disposable component can be a single disposable component that receives the reusable electronics module. In other embodiments, the reusable electronics module can include a reusable electrode (made, e.g., from a conductive fabric or elastomer), and the disposable component can be a simple adhesive component that adheres the reusable electrode to the patient.

In preferred embodiments the patch is worn on the chest, and thus includes both rigid and flexible circuitry, as described above. In other embodiments, the patch only includes rigid circuitry and is designed to fit on other portions of the patient's body that is more flat (e.g. the shoulder).

In embodiments, for example, the system described above can calibrate the patch or necklace for future use. For example, the Floormat can determine a patient-specific relationship between transit time and blood pressure, along with initial values of SYS, DIA, and MAP. Collectively these parameters represent a cuff-based calibration for blood pressure, which can be used by the patch or necklace for cuffless measurements of blood pressure. In other embodiments, the Floormat can measure a full-body impedance measurement and weight. These parameters can be wirelessly transmitted to the necklace or patch, where they are used with their impedance measurement to estimate full-body impedance (e.g. during a dialysis session). Additionally, during the dialysis session, the necklace or patch can use the values of full-body impedance and weight to estimate a progression towards the patient's dry weight.

These and still other embodiments of the invention are deemed to be within the scope of the following claims.

What is claimed is:

1. A system for measuring a user's cardiac output value, comprising:
    a Floormat configured to rest on a flat surface and comprising at least two electrodes and at least one load cell, the load cell further configured to generate a force waveform;
    a Handheld Sensor connected to the Floormat through a cable and comprising at least two electrodes;
    an analog impedance system connected to the at least two electrodes in the Floormat and to the at least two electrodes in the Handheld Sensor, the analog impedance system configured to inject electrical current into the user through one electrode in the Floormat and one electrode in the Handheld Sensor, and further configured to sense signals through one electrode in the Floormat and one electrode in the Handheld Sensor, and in response generate an impedance waveform and an ECG waveform;
    a first processing system configured to process a digitized version of the force waveform to determine a weight value;
    a second processing system configured to process a digitized version of the impedance waveform to determine an impedance pulse, and to further process the impedance pulse to determine values of left ventricular ejection time (LVET) and $(d\Delta Z/dt)_{max}$, and to further process the impedance waveform to determine a value of $Z_0$, and to further process the weight value to determine a volume conductor ($V_c$), and to determine a stroke volume value from the values of LVET, $(d\Delta Z/dt)_{max}$, $Z_0$, and $V_c$,
    a third processing system configured to process a digitized version of the ECG waveform to determine an ECG pulse, and to further process the ECG pulse to determine a heart rate value; and
    a fourth processing system configured to collectively process the stroke volume value and heart rate value to determine the cardiac output value.

2. The system of claim 1, wherein the at least two electrodes in the Floormat are disposed on a top surface of the Floormat and configured to contact the user's foot when the user stands on the Floormat.

3. The system of claim 1, wherein the at least two electrodes in the Floormat comprise at least one of the following: a conductive fabric, a metal, a conductive foam, a hydrogel material, a conductive ink, a conductive rubber.

4. The system of claim 1, wherein the at least two electrodes in the Handheld Sensor are disposed on a grip connected to the Handheld Sensor and configured to contact the user's hand when the user holds the Handheld Sensor.

5. The system of claim 4, wherein the at least two electrodes in the Handheld Sensor comprise at least one of the following: a conductive fabric, a metal, a conductive foam, a hydrogel material, a conductive ink, a conductive rubber.

6. The system of claim 1, wherein the cable comprises a set of conducting wires.

7. The system of claim 6, wherein the conducting wires connect the at least two electrodes in the Handheld Sensor to the analog impedance system.

8. The system of claim 7, wherein the Floormat comprises a circuit board, and the circuit board comprises the analog impedance system.

9. The system of claim 6, wherein the conducting wires connect the at least two electrodes in the Floormat to the analog impedance system.

10. The system of claim 9, wherein the Handheld Sensor comprises a circuit board, and the circuit board comprises the analog impedance system.

11. The system of claim 1, wherein the cable is a flexible cable.

12. The system of claim 1, wherein the cable is a retractable cable that retracts into the Floormat.

13. The system of claim 1, wherein the ECG pulse is an ECG QRS complex.

14. The system of claim 13, wherein the third processing system is further configured to calculate heart rate from a temporal difference separating neighboring ECG QRS complexes.

15. The system of claim 14, wherein the fourth processing system is further configured to calculate the cardiac output value from a product of the stroke volume value and the heart rate value.

16. A system for measuring a user's cardiac output value, comprising:
   a Floormat configured to rest on a flat surface and comprising at least two electrodes and at least one load cell, the load cell further configured to generate a force waveform;
   a Handheld Sensor connected to the Floormat through a cable and comprising at least two electrodes;
   an analog impedance system connected to the at least two electrodes in the Floormat and to the at least two electrodes in the Handheld Sensor, the analog impedance system configured to inject electrical current into the user through one electrode in the Floormat and one electrode in the Handheld Sensor, and further configured to sense signals through one electrode in the Floormat and one electrode in the Handheld Sensor, and in response generate an impedance waveform and an ECG waveform;
   a first processing system configured to process a digitized version of the force waveform to determine a weight value;
   a second processing system configured to process a digitized version of the impedance waveform to determine an impedance pulse, and to further process the impedance pulse to determine values of left ventricular ejection time (LVET) and $(d\Delta Z/dt)_{max}$, and to further process the impedance waveform to determine a value of $Z_0$, and to further process the weight value to determine a volume conductor ($V_c$), and to determine a stroke volume (SV) value from the equation:

$$SV = V_C \times \frac{(d\Delta Z/dt)_{max}}{Z_0} \times LVET$$

or a mathematical equivalent thereof;
   a third processing system configured to process a digitized version of the ECG waveform to determine an ECG pulse, and to further process the ECG pulse to determine a heart rate value; and
   a fourth processing system configured to collectively process the stroke volume value and heart rate value to determine the cardiac output value.

17. The system of claim 16, wherein the at least two electrodes in the Floormat are disposed on a top surface of the Floormat and configured to contact the user's foot when the user stands on the Floormat.

18. The system of claim 16, wherein the at least two electrodes in the Floormat comprise at least one of the following: a conductive fabric, a metal, a conductive foam, a hydrogel material, a conductive ink, a conductive rubber.

19. The system of claim 16, wherein the at least two electrodes in the Handheld Sensor are disposed on a grip connected to the Handheld Sensor and configured to contact the user's hand when the user holds the Handheld Sensor.

20. The system of claim 19, wherein the at least two electrodes in the Handheld Sensor comprise at least one of the following: a conductive fabric, a metal, a conductive foam, a hydrogel material, a conductive ink, a conductive rubber.

21. The system of claim 16, wherein the cable comprises a set of conducting wires.

22. The system of claim 21, wherein the conducting wires connect the at least two electrodes in the Handheld Sensor to the analog impedance system.

23. The system of claim 22, wherein the Floormat comprises a circuit board, and the circuit board comprises the analog impedance system.

24. The system of claim 21, wherein the conducting wires connect the at least two electrodes in the Floormat to the analog impedance system.

25. The system of claim 24, wherein the Handheld Sensor comprises a circuit board, and the circuit board comprises the analog impedance system.

26. The system of claim 16, wherein the cable is a flexible cable.

27. The system of claim 16, wherein the cable is a retractable cable that retracts into the Floormat.

28. The system of claim 16, wherein the ECG pulse is an ECG QRS complex.

29. The system of claim 28, wherein the third processing system is further configured to calculate heart rate from a temporal difference separating neighboring ECG QRS complexes.

30. The system of claim 29, wherein the fourth processing system is further configured to calculate the cardiac output value from a product of the stroke volume value and the heart rate value.

* * * * *